(12) United States Patent
Fotsch et al.

(10) Patent No.: US 8,791,147 B2
(45) Date of Patent: *Jul. 29, 2014

(54) CALCIUM RECEPTOR MODULATING AGENTS

(75) Inventors: Christopher Fotsch, Thousand Oaks, CA (US); Paul Harrington, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 360 days.

This patent is subject to a terminal disclaimer.

(21) Appl. No.: 13/123,468

(22) PCT Filed: Oct. 7, 2009

(86) PCT No.: PCT/US2009/059876
§ 371 (c)(1),
(2), (4) Date: Jun. 6, 2011

(87) PCT Pub. No.: WO2010/042642
PCT Pub. Date: Apr. 15, 2010

(65) Prior Publication Data
US 2011/0230517 A1 Sep. 22, 2011

Related U.S. Application Data

(60) Provisional application No. 61/195,591, filed on Oct. 8, 2008.

(51) Int. Cl.
*A61K 31/44* (2006.01)
*C07D 211/72* (2006.01)
*C07D 211/84* (2006.01)
*C07D 213/62* (2006.01)
*C07D 213/78* (2006.01)
*C07D 211/70* (2006.01)
*C07D 211/82* (2006.01)
*C07D 213/24* (2006.01)

(52) U.S. Cl.
USPC ............ 514/351; 514/357; 546/300; 546/334

(58) Field of Classification Search
CPC ..... A61K 31/44; A61K 31/47; C07D 491/00; C07D 498/00; C07D 513/00; C07D 515/00; C07D 471/00
See application file for complete search history.

(56) References Cited

U.S. PATENT DOCUMENTS

| 5,981,599 | A | 11/1999 | Moe et al. |
| 6,011,068 | A | 1/2000 | Nemeth et al. |
| 6,031,003 | A | 2/2000 | Nemeth et al. |
| 6,313,146 | B1 | 11/2001 | Van Wagenen et al. |
| 6,403,832 | B1 | 6/2002 | Oikawa et al. |
| 6,407,111 | B1 | 6/2002 | Bos et al. |
| 6,436,152 | B1 | 8/2002 | Chassot et al. |
| 6,894,190 | B2 | 5/2005 | Oikawa et al. |
| 6,908,935 | B2 * | 6/2005 | Kelly et al. ................... 514/340 |
| 7,084,167 | B2 | 8/2006 | Ruat et al. |
| 7,157,498 | B2 | 1/2007 | Dauban et al. |
| 7,524,873 | B2 * | 4/2009 | Kelly et al. ................... 514/340 |
| 2007/0225296 | A1 | 9/2007 | Miyazaki et al. |

FOREIGN PATENT DOCUMENTS

| EP | 1466888 | 10/2004 |
| JP | 2002030050 | 1/2002 |
| WO | WO 01/90069 | 11/2001 |
| WO | WO 03/099776 A1 * | 12/2003 |
| WO | WO 2004/030669 | 4/2004 |
| WO | WO 2007/124465 | 11/2007 |
| WO | WO 2007/124465 A * | 11/2007 |
| WO | WO 2008/019690 A1 * | 2/2008 |
| WO | WO 2008/035381 | 3/2008 |
| WO | WO 2009/051718 | 4/2009 |

OTHER PUBLICATIONS

Carmona, D. et al. Pentamethylcyclopentadienyl-iridium(III) complexes with pyridylamino ligands: synthesis and applications as asymmetric catalysts for Diels-Alder reactions. Dalton Transactions. 2007, p. 1911, left column, figures.*
Brown et al., "Neomycin mimics the effects of high extracellular calcium concentrations on parathyroid function in dispersed bovine parathyroid cells." Endocrinology, vol. 128, No. 6. 3047-3054, 1991.
Chen et al,. "The diltiazem TA-3090 mimics the actions of high extracellular Ca2* on parathyroid function in dispersed bovine parathyroid cells." Journal of Bone and Mineral Research. vol. 5. No. 6. 581-587, 1990.
Dauban et al,. "N1-Arylsulfonyl-N2-(1-aryl)ethyl-3-phenylpropane-1,2-diamines as novel calcimimetics acting on the calcium sensing receptor," Biorg. Med. Chem. Lett., 10, 2001-2004, 2000.
Didiuek et al., "Short-acting. 5-(trifluoromethyl)pyrido[4,3-d]pyrimidin-4(3H)-one derivatives as orally-active calcium-sensing receptor antagonists," Biorg. Med. Chem. Lett., 19. 4555-4559, 2009.
Garrett et al., "Calcitonin-secreting cells of the thyroid express an extracellular calcium receptor gene," Endocrinology, vol. 136, No. 11, 5202-5211, 1995.
Garrett et al., "Molecular cloning and functional expression of human parathyroid calcium receptor DNAs," Journal of Biological Chemistry, vol. 270, No. 21, 12919-12925, 1995.
Nemeth et al., "Regulation of cytosolic calcium by extracellulary divalent cations in c-cells and parathyroid cells," Cell Calcium, vol. 11, 323-327, 1990.

(Continued)

*Primary Examiner* — Rita Desai
*Assistant Examiner* — Ben S Michelson
(74) *Attorney, Agent, or Firm* — Olga Mekhovich

(57) ABSTRACT

The present invention relates generally to novel calcimimetic compounds and pharmaceutical compositions comprising them. The invention also relates to methods of treating of diseases or disorders related to the function of the calcium sensing receptor using the compounds represented in Formula (I). Where $Cy^1$ is pyridinonyl, pyridinyl, quinolinyl or 9-ethyl-9H-beta-carbolinyl, each of which optionally substituted and where $Cy^2$ is phenyl naphthyl.

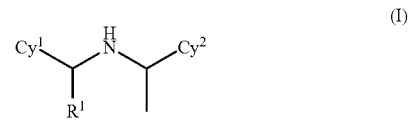

2 Claims, No Drawings

(56) References Cited

OTHER PUBLICATIONS

Nemeth et al., "Calcimimetics with potent and selective activity on the parathyroid calcium receptor," Pharmacology, vol. 95. 4040-4045, 1998.

Svensson et al., "The design and bioactivation of presystematically stable prodrugs." Drug Metabolism Reviews. 19(2), 165-194, 1988.

Zaidi et al., "Intracellular calcium in the control of osteoclast function," Biochemical and Biophysical Research Cormmunications, vol. 167, No. 2, 807-812, 1990.

Zaidi et al., "Calcium receptors on eukaryotic cells with special reference to the osteoclast," Bioscience Reports, vol. 10, No. 6. 493-507, 1990.

* cited by examiner

CALCIUM RECEPTOR MODULATING AGENTS

FIELD OF THE INVENTION

This invention relates generally to the field of medicine and, more specifically, to calcium receptor modulating compounds and pharmaceutical compositions comprising them.

BACKGROUND OF THE INVENTION

Extracellular calcium ion concentration is involved in a variety of biological processes, such as blood clotting, nerve and muscle excitability and bone formation (Cell Calcium 11:319, 1990). One of the key elements of this regulation is the calcium receptor known as the Ca sensing receptor (CaSR). Calcium ion receptors, which are present on the membranes of various cells in the body, such as parathyroid and kidney cells (Nature 366:574, 1993; J. Bone Miner. Res. 9, Supple. 1, s282, 1994; J. Bone Miner. Res. 9, Supple. 1, s409, 1994; Endocrinology 136:5202, 1995), are important to the regulation of the extracellular calcium ion concentration. For example, concentration of extracellular calcium ion regulates the bone resorption by osteoclasts (Bioscience Reports 10:493, 1990), secretion of parathyroid hormone (PTH) from parathyroid cells and secretion of calcitonin from C-cells (Cell Calcium 11:323, 1990). Parathyroid cells thus have at their surface the calcium sensing receptor (CaSR), which detects changes in extracellular calcium concentration and initiates the functional response of this cell, which is a modulation of the secretion of the parathyroid hormone (PTH). Secretion of PTH increases extracellular calcium ion concentration by acting on various cells, such as bone and kidney cells, and the extracellular calcium ion concentration reciprocally inhibits the secretion of PTH by acting on parathyroid cells. The reciprocal relationship between calcium concentration and PTH level is an essential mechanism for calcium homeostasis maintenance.

The cloning of the calcium receptor by Brown in 1993 consequently demonstrated two possible signalling pathways for this G protein coupled receptor: one pathway by activation of the Gi protein (sensitive to the pertussis toxin) which stimulates phospholipase C and inhibits adenylate cyclase; the other pathway by activating the Gq protein responsible for mobilising intracellular calcium. These two signalling pathways, either independently of one another or together, can be activated so as to trigger the associated biological effect. On its extracellular portion, the calcium receptor is a low affinity receptor which is stimulated by millimolar concentrations of agonists, in particular the calcium ion $Ca^{2+}$. In addition, this receptor can also be activated by some divalent metals (magnesium) or trivalent metals (gadolinium, lanthanum, etc.) or else by polycationic compounds such as neomycin or spermine.

Several classes of calcimimetic compounds have been disclosed for regulating extracellular calcium ion concentration, particularly for reducing or inhibiting secretion of PTH. For example, U.S. Pat. Nos. 6,011,068 and 5,981,599 disclose arylalkylamines that are calcium receptor active molecules. EP 933354; WO 0021910, WO 96/12697; WO 95/11221; WO 94/18959; WO 93/04373; WO 06/123725, AU 2004202208, Endocrinology 128:3047, 1991; Biochem. Biophys. Res. Commun. 167:807, 1990; J. Bone Miner. Res. 5:581, 1990; and Nemeth et al., "Calcium-binding Proteins in Health and Disease," Academic Press, Inc., pp. 33-35 (1987) disclose various agents that interact with calcium receptors.

Dauban et al., Bioorg. Med. Chem. Let. 10:2001-4, 2000, disclose various N1-arylsulfonyl-N2-(1-aryl)ethyl-3-phenyl-propane-1,2-diamine compounds as calcimimetics acting on the calcium sensing receptor.

Oikawa et al., in U.S. Pat. No. 6,403,832, and publication No. US2002/143212, describes aryl amine compounds useful as chiral intermediates in the synthesis of optically active propionic acid derivatives. Chassot et al., U.S. Pat. No. 6,436,152, describes arylalkylamine compounds useful as hair dye precursor compounds. Other calcimimetic compounds are disclosed in U.S. Pat. Nos. 6,313,146; 6,001,884; PCT publications WO 01/34562; WO 01/90069; WO 02/059102; WO 02/12181; WO 05/115975; WO 06/117211; WO 06/123725; WO 08/059,854; WO 08/019,690; WO 08/057,282.

SUMMARY OF THE INVENTION

The present invention relates to selected calcimimetic compounds and pharmaceutically acceptable salts thereof. This invention also encompasses pharmaceutical compositions, methods for reducing or inhibiting PTH secretion and methods for treatment or prophylaxis of diseases associated with excessive secretion of PTH, such as hyperparathyroidism. Thus, in one aspect, the invention compounds advantageously reduce or inhibit PTH secretion. In another aspect, the compounds of the invention are useful for treatment of other diseases and disorders associated with the function of the calcium sensing receptor, such as vascular calcification, polycystic kidney disease, podocyte-related disorders and inflammatory bowel disorders.

In one aspect, the invention provides compounds or pharmaceutically acceptable salts thereof, wherein the compounds are selected from the group consisting of:

1-(5-methoxy-6-(4-(trifluoromethyl)phenyl)-2-pyridinyl)-N-((1R)-1-phenylethyl)ethanamine, (1R)—N-((5-chloro-6-(3-fluorophenyl)-2-pyridinyl)methyl)-1-(3-chlorophenyl)ethanamine, (1R)—N-((2-(4-methoxyphenyl)-4-pyridinyl)methyl)-1-(1-naphthalenyl)ethanamine, (1R)—N-((5-methoxy-6-(4-(trifluoromethyl)phenyl)-2-pyridinyl)methyl)-1-phenylethanamine, (1R)—N-((9-ethyl-9H-beta-carbolin-3-yl)methyl)-1-(1-naphthalenyl)ethanamine, (1R)-1-(3-chlorophenyl)-N-((6-methoxy-5-(4-(trifluoromethyl)phenyl)-3-pyridinyl)methyl)ethanamine, (1R)-1-(3-methoxyphenyl)-N-(2-quinolinylmethyl)ethanamine, (1R)-1-(1-naphthalenyl)-N-(2-quinolinylmethyl)ethanamine, (1R)-1-(3-chlorophenyl)-N-((6-(3-fluorophenyl)-5-methoxy-2-pyridinyl)methyl)ethanamine, (1R)—N-((5-chloro-4-(3-fluorophenyl)-2-pyridinyl)methyl)-1-(3-chlorophenyl)ethanamine, (1R)-1-(3-methoxyphenyl)-N-((2-(4-methoxyphenyl)-4-pyridinyl)methyl)ethanamine, (1R)—N-((2,6'-dimethoxy-3,3'-bipyridin-5-yl)methyl)-1-phenylethanamine, (1R)-1-(1-naphthalenyl)-N-(2-quinolinylmethyl)ethanamine, (1R)-1-(3-methoxyphenyl)-N-(3-quinolinylmethyl)ethanamine, (1R)—N-((9-ethyl-9H-beta-carbolin-3-yl)methyl)-1-phenylethanamine, 1-(6-methoxy-4'-(trifluoromethyl)-3-biphenylyl)-N-((1R)-1-(2-pyridinyl)ethyl)ethanamine, (1R)-1-(1-naphthalenyl)-N-(3-quinolinylmethyl)ethanamine, (1R)—N-((6-methoxy-5-(4-(trifluoromethyl)phenyl)-3-pyridinyl)methyl)-1-phenylethanamine,
(1R)—N-(2,3'-bipyridin-4-ylmethyl)-1-(1-naphthalenyl)ethanamine,
(1R)-1-(3-fluorophenyl)-N-((6-methoxy-5-(4-(trifluoromethyl)phenyl)-3-pyridinyl)methyl)ethanamine,
(1R)—N-((2-(4-methoxyphenyl)-4-pyridinyl)methyl)-1-phenylethanamine,
(1R)—N-((2-methoxy-6'-(2,2,2-trifluoroethoxy)-3,3'-bipyridin-5-yl)methyl)-1-phenylethanamine,
(1R)—N-((6-((6-fluoro-3-pyridinyl)methoxy)-3-pyridinyl)methyl)-1-(1-naphthalenyl)ethanamine,
(1R)-1-(3-methoxyphenyl)-N-(3-quinolinylmethyl)ethanamine,
(1R)-1-(1-naphthalenyl)-N-((6-phenoxy-3-pyridinyl)methyl)ethanamine,
(1R)—N-((9-ethyl-9H-beta-carbolin-3-yl)methyl)-1-(3-methoxyphenyl)ethanamine,
(1R)—N-((6-methyl-2-pyridinyl)methyl)-1-(1-naphthalenyl)ethanamine,
(1R)-1-(1-naphthalenyl)-N-(4-pyridinylmethyl)ethanamine,
1-(4-fluorophenyl)-5-((((1R)-1-(1-naphthalenyl)ethyl)amino)methyl)-2(1H)-pyridinone,
(1R)—N-((6-((4-chlorophenyl)sulfanyl)-3-pyridinyl)methyl)-1-(1-naphthalenyl)ethanamine,
(1R)-1-(3-methoxyphenyl)-N-((6-phenoxy-3-pyridinyl)methyl)ethanamine,
1-(4-methoxyphenyl)-5-((((1R)-1-phenylethyl)amino)methyl)-2(1H)-pyridinone,
(1R)—N-((6-fluoro-5-(4-(trifluoromethyl)phenyl)-3-pyridinyl)methyl)-1-phenylethanamine,
2'-fluoro-5'-((((1R)-1-phenylethyl)amino)methyl)-N-(tetrahydro-2-furanylmethyl)-3,3'-bipyridin-6-amine,
(1R)—N-((6-((6-methoxy-3-pyridinyl)methoxy)-3-pyridinyl)methyl)-1-phenylethanamine,
(1R)—N-((6-((6-methoxy-3-pyridinyl)methoxy)-3-pyridinyl)methyl)-1-(1-naphthalenyl)ethanamine,
(1R)—N-((6-((6-fluoro-3-pyridinyl)methoxy)-3-pyridinyl)methyl)-1-phenylethanamine,
(1R)—N-((2-methoxy-6'-(tetrahydro-2-furanylmethoxy)-3,3'-bipyridin-5-yl)methyl)-1-phenylethanamine,
(1R)-1-(1-naphthalenyl)-N-(3-pyridinylmethyl)ethanamine,
(1R)—N-((6-methyl-2-pyridinyl)methyl)-1-(1-naphthalenyl)ethanamine,
(1R)-1-(3-methoxyphenyl)-N-(2-pyridinylmethyl)ethanamine,
(1R)-1-(3-methoxyphenyl)-N-(2-quinolinylmethyl)ethanamine,
(1R)-1-(1-naphthalenyl)-N-(2-pyridinylmethyl)ethanamine,
6-((((1R)-1-(3-methoxyphenyl)ethyl)amino)methyl)-2-(methylsulfanyl)-3-pyridinecarbonitrile,
(1R)—N-((6-((2-chlorophenyl)sulfanyl)-3-pyridinyl)methyl)-1-(1-naphthalenyl)ethanamine,
(1R)—N-((2-chloro-4-pyridinyl)methyl)-1-(1-naphthalenyl)ethanamine,
(1R)—N-((2-(4-chlorophenoxy)-3-pyridinyl)methyl)-1-phenylethanamine,
2-(methylsulfanyl)-6-((((1R)-1-phenylethyl)amino)methyl)-3-pyridinecarbonitrile,
2'-methoxy-5'-((((1R)-1-phenylethyl)amino)methyl)-N-(tetrahydro-2-furanylmethyl)-3,3'-bipyridin-6-amine,
(1R)-1-(3-methoxyphenyl)-N-(3-pyridinylmethyl)ethanamine,
(1R)-1-(3-methoxyphenyl)-N-((6-methyl-2-pyridinyl)methyl)ethanamine,
(1R)-1-(3-methoxyphenyl)-N-(4-quinolinylmethyl)ethanamine,
(1R)—N-((6-((4-chlorophenyl)sulfanyl)-3-pyridinyl)methyl)-1-phenylethanamine,
(1R)—N-((2-chloro-4-pyridinyl)methyl)-1-(3-methoxyphenyl)ethanamine,
(1R)-1-(3-methoxyphenyl)-N-(2-pyridinylmethyl)ethanamine,
(1R)-1-(4-methylphenyl)-N-(2-pyridinylmethyl)ethanamine,
(1R)-1-(4-methylphenyl)-N-(3-quinolinylmethyl)ethanamine,
or a pharmaceutically acceptable salt thereof.

In another aspect, the invention provides methods for treating a patient in need of such treatment comprising the step of administering to the patient a therapeutically effective amount of a compound of Formula I

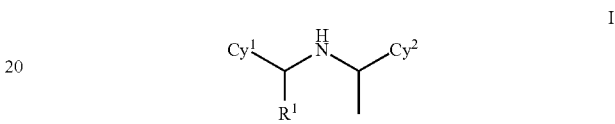

or a pharmaceutically acceptable salt thereof, wherein all substituents are as described in Detailed Description below.

In one aspect, the patient has a disease characterized by abnormal calcium homeostasis. In one aspect, the disease is hyperparathyroidism. In another aspect, the disease is vascular calcification. In a further aspect, the disease can be a polycystic kidney disorder. In another aspect, the disease can be an abnormal intestinal motility, such as diarrhea. In a further aspect, the disease may be a podocyte-related disorder. In one aspect, the disease or disorder can be malassimilation or malnutrition. In another aspect, the disease can be inflammatory bowel disease or irritable bowel syndrome.

The invention also provides pharmaceutical compositions comprising the compounds of the invention or a pharmaceutically acceptable salt thereof and a pharmaceutically acceptable diluent or carrier.

DETAILED DESCRIPTION OF THE INVENTION

I. Definitions

"Treating" or "treatment" of a disease includes: (1) preventing the disease, i.e., causing the clinical symptoms of the disease not to develop in a subject that may be or has been exposed to the disease or conditions that may cause the disease, or predisposed to the disease but does not yet experience or display symptoms of the disease, (2) inhibiting the disease, i.e., arresting or reducing the development of the disease or any of its clinical symptoms, or (3) relieving the disease, i.e., causing regression of the disease or any of its clinical symptoms.

The phrase "therapeutically effective amount" is the amount of the compound of the invention that will achieve the goal of prevention of the disorder or improvement in disorder severity and the frequency of incidence. The improvement in disorder severity includes the reversal of the disease, as well as slowing down the progression of the disease.

As used herein, "calcium sensing receptor" or "CaSR" refers to the G-protein-coupled receptor responding to changes in extracellular calcium and/or magnesium levels. Activation of the CaSR produces rapid, transient increases in cytosolic calcium concentration by mobilizing calcium from thapsigargin-sensitive intracellular stores and by increasing calcium influx though voltage-insensitive calcium channels in the cell membrane (Brown et al., Nature 366: 575-580, 1993; Yamaguchi et al., *Adv Pharmacol* 47: 209-253, 2000).

Unless otherwise specified, the following definitions apply to terms found in the specification and claims:

The term "alkyl" by itself or as part of another substituent, means, unless otherwise stated, a straight or branched chain, or cyclic, saturated hydrocarbon having the indicated number of carbon atoms (i.e., $C_1$-$C_8$ means one to eight carbons). For example, $C_{1-8}$ alkyl is meant to include, but is not limited to methyl, ethyl, propyl, isopropyl, butyl, sec-butyl, tert-butyl, pentyl, isopentyl, neopentyl, hexyl, isohexyl, cyclohexyl, cyclohexylmethyl, cyclopropylmethyl and neohexyl.

The term "alkenyl" as used herein refers to a straight or branched chain unsaturated hydrocarbon having the indicated number of carbon atoms (i.e., $C_{2-8}$ means two to eight carbons) and at least one double bond. Examples of a $C_{2-8}$ alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene.

The term "alkylene" refers to a divalent alkyl group (e.g., an alkyl group attached to two other moieties, typically as a linking group). Examples of a $C_{1-8}$ alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. The term "alkenylene" refers to a divalent alkenyl group (e.g., an alkenyl group attached to two other moieties, typically as a linking group). Examples of a $C_{2-8}$ alkenylene group include —CH=CH—, —$CH_2$CH=CH—, —$CH_2$CH=$CHCH_2$—, as well as branched versions thereof.

Typically, an alkyl, alkenyl, alkylene, or alkenylene group will have from 1 to 24 carbon atoms, with those groups having 10 or fewer carbon atoms being preferred in the present invention. A "lower alkyl" "lower alkenyl" or "lower alkylene" is a shorter chain alkyl or alkylene group, generally having eight or fewer carbon atoms.

The term "heteroatom" is meant to include oxygen (O), nitrogen (N), sulfur (S) and silicon (Si).

The term "cycloalkyl" by itself or in combination with other terms, represents, unless otherwise stated, cyclic version of "alkyl". Thus, the term "cycloalkyl" is meant to be included in the terms "alkyl". Examples of cycloalkyl include cyclopentyl, cyclohexyl, 1-cyclohexenyl, 3-cyclohexenyl, cycloheptyl, cyclobutylene, cyclohexylene and the like.

The term "aryl" as used herein refers to a 6- to 14-membered monocyclic, bicyclic or tricyclic aromatic hydrocarbon ring system. Examples of an aryl group include phenyl and naphthyl.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl. A heteroaryl group can be unsubstituted or optionally substituted with one or more substituents as described herein below.

The term "alkoxy" as used herein refers to an —O-alkyl group. For example, an alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl. The term "alkoxyalkyl" refers to an alkoxy group appended to an alkyl radical. The term "aryloxy" as used herein refers to an —O-aryl group. The term "alkoxyaryl" refers to an alkoxy group attached to an aryl radical.

The term "amino" refers to a chemical functionality —NR'R", wherein R' and R" are independently hydrogen, alkyl or aryl.

The term "halo" or "halogen" as used herein refers to —F, —Cl, —Br or —I.

The term "haloalkyl," as used herein, refers to a $C_1$-$C_6$ alkyl group wherein one or more of the $C_1$-$C_6$ alkyl group's hydrogen atoms is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl. Thus, the term "haloalkyl" includes monohaloalkyl (alkyl substituted with one halogen atom) and polyhaloalkyl (alkyl substituted with halogen atoms in a number ranging from two to (2 m'+1) halogen atoms, where m' is the total number of carbon atoms in the alkyl group).

The term "protected" with respect to hydroxyl groups, amine groups, carboxyl groups and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., ($3^{rd}$ Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The compounds of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of the compounds of the invention, including tautomeric forms of the compound.

Certain compounds of the invention may have asymmetric centers and therefore exist in different enantiomeric and diastereomeric forms. A compound of the invention can be in the form of an optical isomer or a diastereomer. Accordingly, the invention encompasses calcium-sensing receptor modulators and their uses as described herein in the form of their optical isomers, and mixtures thereof, including a racemic mixture.

Optical isomers of the calcium-sensing receptor modulators can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester, but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, e.g., cancer therapeutic agents, research reagents, e.g., assay reagents, and diagnostic agents, e.g., in vivo imaging agents. All isotopic variations of the compounds of the invention, whether radioactive or not, are intended to be encompassed within the scope of the invention.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

II. Compounds that Modulate Calcium Sensing Receptor and Pharmaceutical Compositions Comprising them, Administration and Dosage As used herein, the term "calcimimetic compound" or "calcimimetic" refers to a compound that binds to calcium sensing receptors and induces a conformational change that reduces the threshold for calcium sensing receptor activation by the endogenous ligand $Ca^{2+}$. These calcimimetic compounds can also be considered allosteric modulators of the calcium receptors.

In one aspect, a calcimimetic can have one or more of the following activities: it evokes a transient increase in internal calcium, having a duration of less than 30 seconds (for example, by mobilizing internal calcium); it evokes a rapid increase in $[Ca^{2+}]_i$ occurring within thirty seconds; it evokes a sustained increase (greater than thirty seconds) in $[Ca^{2+}]_i$ (for example, by causing an influx of external calcium); evokes an increase in inositol-1,4,5-triphosphate or diacylglycerol levels, usually within less than 60 seconds; and inhibits dopamine- or isoproterenol-stimulated cyclic AMP formation. In one aspect, the transient increase in $[Ca^{2+}]_i$ can be abolished by pretreatment of the cell for ten minutes with 10 mM sodium fluoride or with an inhibitor of phospholipase C, or the transient increase is diminished by brief pretreatment (not more than ten minutes) of the cell with an activator of protein kinase C, for example, phorbol myristate acetate (PMA), mezerein or (−) indolactam V.

While the compounds of the invention are believed to exert their effects by interacting with the calcium sensing receptor (CaSR), the mechanism of action by which the compounds act is not a limiting embodiment of the invention. For example, compounds of the invention may interact with calcium sensing receptors other than CaSR.

Compounds contemplated by the invention include, but are not limited to, the exemplary compounds provided herein.

In certain embodiments, the calcimimetic compound is chosen from the following compounds or pharmaceutically acceptable salts thereof:

1-(5-methoxy-6-(4-(trifluoromethyl)phenyl)-2-pyridinyl)-N-((1R)-1-phenylethyl)ethanamine,
(1R)—N-((5-chloro-6-(3-fluorophenyl)-2-pyridinyl)methyl)-1-(3-chlorophenyl)ethanamine,
(1R)—N-((2-(4-methoxyphenyl)-4-pyridinyl)methyl)-1-(1-naphthalenyl)ethanamine,
(1R)—N-((5-methoxy-6-(4-(trifluoromethyl)phenyl)-2-pyridinyl)methyl)-1-phenylethanamine,
(1R)—N-((9-ethyl-9H-beta-carbolin-3-yl)methyl)-1-(1-naphthalenyl)ethanamine,
(1R)-1-(3-chlorophenyl)-N-((6-methoxy-5-(4-(trifluoromethyl)phenyl)-3-pyridinyl)methyl)ethanamine,
(1R)-1-(3-methoxyphenyl)-N-(2-quinolinylmethyl)ethanamine,
(1R)-1-(1-naphthalenyl)-N-(2-quinolinylmethyl)ethanamine,
(1R)-1-(3-chlorophenyl)-N-((6-(3-fluorophenyl)-5-methoxy-2-pyridinyl)methyl)ethanamine,
(1R)—N-((5-chloro-4-(3-fluorophenyl)-2-pyridinyl)methyl)-1-(3-chlorophenyl)ethanamine,
(1R)-1-(3-methoxyphenyl)-N-((2-(4-methoxyphenyl)-4-pyridinyl)methyl)ethanamine,
(1R)—N-((2,6'-dimethoxy-3,3'-bipyridin-5-yl)methyl)-1-phenylethanamine,
(1R)-1-(1-naphthalenyl)-N-(2-quinolinylmethyl)ethanamine,
(1R)-1-(3-methoxyphenyl)-N-(3-quinolinylmethyl)ethanamine,
(1R)—N-((9-ethyl-9H-beta-carbolin-3-yl)methyl)-1-phenylethanamine,
1-(6-methoxy-4'-(trifluoromethyl)-3-biphenylyl)-N-((1R)-1-(2-pyridinyl)ethyl)ethanamine,
(1R)-1-(1-naphthalenyl)-N-(3-quinolinylmethyl)ethanamine,
(1R)—N-((6-methoxy-5-(4-(trifluoromethyl)phenyl)-3-pyridinyl)methyl)-1-phenylethanamine,
(1R)—N-(2,3'-bipyridin-4-ylmethyl)-1-(1-naphthalenyl)ethanamine,
(1R)-1-(3-fluorophenyl)-N-((6-methoxy-5-(4-(trifluoromethyl)phenyl)-3-pyridinyl)methyl)ethanamine,
(1R)—N-((2-(4-methoxyphenyl)-4-pyridinyl)methyl)-1-phenylethanamine,
(1R)—N-((2-methoxy-6'-(2,2,2-trifluoroethoxy)-3,3'-bipyridin-5-yl)methyl)-1-phenylethanamine,
(1R)—N-((6-((6-fluoro-3-pyridinyl)methoxy)-3-pyridinyl)methyl)-1-(1-naphthalenyl)ethanamine,
(1R)-1-(3-methoxyphenyl)-N-(3-quinolinylmethyl)ethanamine,
(1R)-1-(1-naphthalenyl)-N-((6-phenoxy-3-pyridinyl)methyl)ethanamine,
(1R)—N-((9-ethyl-9H-beta-carbolin-3-yl)methyl)-1-(3-methoxyphenyl)ethanamine,
(1R)—N-((6-methyl-2-pyridinyl)methyl)-1-(1-naphthalenyl)ethanamine,
(1R)-1-(1-naphthalenyl)-N-(4-pyridinylmethyl)ethanamine,
1-(4-fluorophenyl)-5-((((1R)-1-(1-naphthalenyl)ethyl)amino)methyl)-2(1H)-pyridinone,
(1R)—N-((6-((4-chlorophenyl)sulfanyl)-3-pyridinyl)methyl)-1-(1-naphthalenyl)ethanamine,
(1R)-1-(3-methoxyphenyl)-N-((6-phenoxy-3-pyridinyl)methyl)ethanamine,
1-(4-methoxyphenyl)-5-((((1R)-1-phenylethyl)amino)methyl)-2(1H)-pyridinone,
(1R)—N-((6-fluoro-5-(4-(trifluoromethyl)phenyl)-3-pyridinyl)methyl)-1-phenylethanamine,
2'-fluoro-5'-((((1R)-1-phenylethyl)amino)methyl)-N-(tetrahydro-2-furanylmethyl)-3,3'-bipyridin-6-amine,
(1R)—N-((6-((6-methoxy-3-pyridinyl)methoxy)-3-pyridinyl)methyl)-1-phenylethanamine,
(1R)—N-((6-((6-methoxy-3-pyridinyl)methoxy)-3-pyridinyl)methyl)-1-(1-naphthalenyl)ethanamine,
(1R)—N-((6-((6-fluoro-3-pyridinyl)methoxy)-3-pyridinyl)methyl)-1-phenylethanamine,
(1R)—N-((2-methoxy-6'-(tetrahydro-2-furanylmethoxy)-3,3'-bipyridin-5-yl)methyl)-1-phenylethanamine,
(1R)-1-(1-naphthalenyl)-N-(3-pyridinylmethyl)ethanamine,
(1R)—N-((6-methyl-2-pyridinyl)methyl)-1-(1-naphthalenyl)ethanamine,
(1R)-1-(3-methoxyphenyl)-N-(2-pyridinylmethyl)ethanamine,
(1R)-1-(3-methoxyphenyl)-N-(2-quinolinylmethyl)ethanamine,
(1R)-1-(1-naphthalenyl)-N-(2-pyridinylmethyl)ethanamine,
6-((((1R)-1-(3-methoxyphenyl)ethyl)amino)methyl)-2-(methylsulfanyl)-3-pyridinecarbonitrile,
(1R)—N-((6-((2-chlorophenyl)sulfanyl)-3-pyridinyl)methyl)-1-(1-naphthalenyl)ethanamine,
(1R)—N-((2-chloro-4-pyridinyl)methyl)-1-(1-naphthalenyl)ethanamine,
(1R)—N-((2-(4-chlorophenoxy)-3-pyridinyl)methyl)-1-phenylethanamine,
2-(methylsulfanyl)-6-((((1R)-1-phenylethyl)amino)methyl)-3-pyridinecarbonitrile,
2'-methoxy-5'-((((1R)-1-phenylethyl)amino)methyl)-N-(tetrahydro-2-furanylmethyl)-3,3'-bipyridin-6-amine,
(1R)-1-(3-methoxyphenyl)-N-(3-pyridinylmethyl)ethanamine,
(1R)-1-(3-methoxyphenyl)-N-((6-methyl-2-pyridinyl)methyl)ethanamine,
(1R)-1-(3-methoxyphenyl)-N-(4-quinolinylmethyl)ethanamine,
(1R)—N-((6-((4-chlorophenyl)sulfanyl)-3-pyridinyl)methyl)-1-phenylethanamine,
(1R)—N-((2-chloro-4-pyridinyl)methyl)-1-(3-methoxyphenyl)ethanamine,
(1R)-1-(3-methoxyphenyl)-N-(2-pyridinylmethyl)ethanamine,
(1R)-1-(4-methylphenyl)-N-(2-pyridinylmethyl)ethanamine, and
(1R)-1-(4-methylphenyl)-N-(3-quinolinylmethyl)ethanamine,
or a pharmaceutically acceptable salt thereof.

In another aspect, the invention incompasses the following compounds:

(1R)-1-(5-methoxy-6-(4-(trifluoromethyl)phenyl)-2-pyridi-nyl)-N-((1R)-1-phenylethyl)ethanamine,
(1R)—N-((5-chloro-6-(3-fluorophenyl)-2-pyridinyl)me-thyl)-1-(3-chlorophenyl)ethanamine,
(1R)—N-((2-(4-methoxyphenyl)-4-pyridinyl)methyl)-1-(1-naphthalenyl)ethanamine,
(1R)—N-((5-methoxy-6-(4-(trifluoromethyl)phenyl)-2-py-ridinyl)methyl)-1-phenylethanamine,
(1R)—N-((9-ethyl-9H-beta-carbolin-3-yl)methyl)-1-(1-naphthalenyl)ethanamine,
(1R)-1-(3-chlorophenyl)-N-((6-methoxy-5-(4-(trifluorom-ethyl)phenyl)-3-pyridinyl)methyl)ethanamine,
(1R)-1-(3-methoxyphenyl)-N-(2-quinolinylmethyl)etha-namine,
(1R)-1-(1-naphthalenyl)-N-(2-quinolinylmethyl)etha-namine,
(1R)-1-(3-chlorophenyl)-N-((6-(3-fluorophenyl)-5-meth-oxy-2-pyridinyl)methyl)ethanamine,
(1R)—N-((5-chloro-4-(3-fluorophenyl)-2-pyridinyl)me-thyl)-1-(3-chlorophenyl)ethanamine, and
(1R)-1-(3-methoxyphenyl)-N-((2-(4-methoxyphenyl)-4-py-ridinyl)methyl)ethanamine,
or a pharmaceutically acceptable salt thereof.

In one aspect, the invention encompasses methods for treating a patient in need of such treatment comprising the step of administering to the patient a therapeutically effective amount of a compound of Formula I

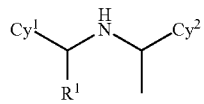

I or a pharmaceutically acceptable salt thereof, wherein:

$Cy^1$ is selected from the group consisted of pyridinonyl, pyridinyl, quinolinyl and 9-ethyl-9H-beta-carbolinyl, each of which can be optionally substituted independently with 1-3 substituents selected from the group consisting of $C_{1-6}$alkyl, $C_{1-4}$haloalkyl, halogen, cyano, amino, $R^a$, —$OC_{1-6}$alkyl, —$OR^a$, —$OC_{1-6}$alkyl-$R^a$, —$SC_{1-6}$alkyl, and —$SR^a$;

$R^a$ is phenyl or pyridyl, either of which can be optionally substituted independently with 1-3 substituents selected from the group consisting of halogen, $C_{1-6}$alkyl, $C_{1-4}$haloalkyl, —$OC_{1-6}$alkyl, tetrahydrofuranylmethylamine, and cyano;

$R^1$ is H or methyl, $Cy^2$ is phenyl or naphthyl, either of which can be optionally substituted with 1-5 substituents, wherein the substituents are selected from the group consisting from $C_{1-6}$alkyl, $C_{1-4}$haloalkyl, halogen, cyano, amino, and —$OC_{1-6}$alkyl.

In one aspect, $Cy^2$ can be optionally substituted phenyl. In one aspect, phenyl can be unsubstituted. In another aspect, phenyl can be substituted with halogen. In a further aspect, phenyl can be substituted with $C_{1-6}$alkyl or $C_{1-4}$haloalkyl.

In another aspect, $Cy^2$ can be optionally substituted naphthyl. For example, naphthyl can be unsubstituted.

In one aspect, $R^1$ can be H. In another aspect, $R^1$ can be $C_{1-3}$alkyl.

The invention provides compounds wherein $Cy^1$ is optionally substituted pyridinonyl. In another aspect, $Cy^1$ can be optionally substituted pyridinyl. In a further aspect, $Cy^1$ can be optionally substituted 9-ethyl-9H-beta-carbolinyl.

A. Preparation of Starting Materials

Starting materials used in preparation of the compounds of the invention were prepared as described in detail below.

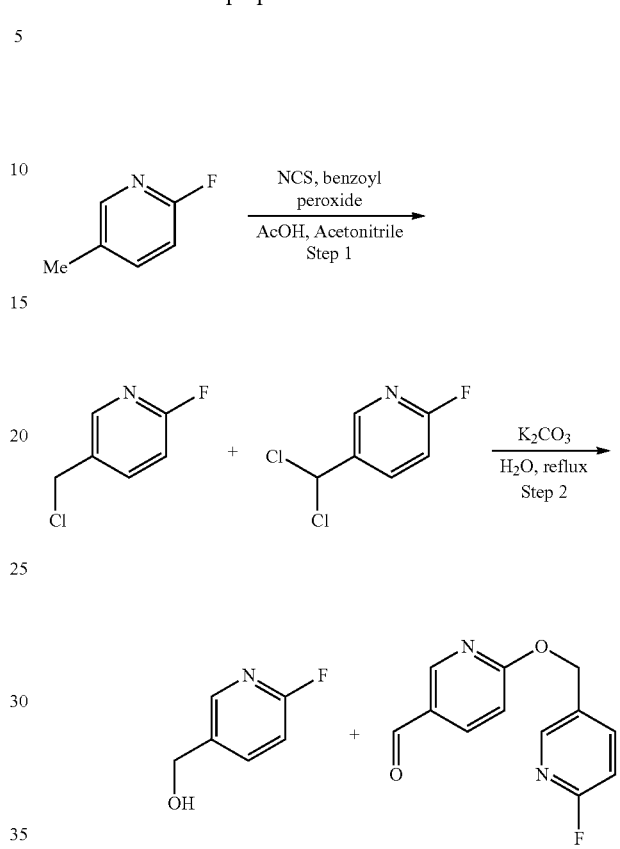

Preparation of (6-fluoropyridin-3-yl)methanol and 6-((6-fluoropyridin-3-yl)methoxy)nicotinaldehyde Step 1. A mixture of 2-fluoro-5-methylpyridine (25.0 g, 225 mmol), N-chlorosuccinimide (45.1 g, 338 mmol), benzoyl peroxide (1.09 g, 4.5 mmol), AcOH (1.0 mL), and acetonitrile (132 mL) was heated at reflux for 5 h. The mixture was then cooled to rt and poured into $H_2O$ (20 mL) and extracted with EtOAc (3×20 mL). The combined organic layers were then washed with 30 mL of a 5% aqueous NaCl solution. The organic layer was then dried over $MgSO_4$, filtered, and concentrated in vacuo to give a mixture of 5-(chloromethyl)-2-fluoropyridine and 5-(dichloromethyl)-2-fluoropyridine as a yellow oil, which was carried onto the next step without further purification.

Step 2. The mixture of 5-(chloromethyl)-2-fluoropyridine and 5-(dichloromethyl)-2-fluoropyridine (30.7 g, 211 mmol) was placed into a round-bottomed flask with $H_2O$ (300 mL) and $K_2CO_3$ (32.1 g, 232 mmol), which was heated to an oily suspension for 4 h. The mixture was then cooled to rt, and the layers were separated. The aqueous layer was washed with EtOAc (2×50 mL). The combined organic layers were then washed with $H_2O$ (3×100 mL), dried over $MgSO_4$, filtered, and concentrated. This mixture was purified by column chromatography (6:1 hexane:EtOAc) to yield (6-fluoropyridin-3-yl)methanol and 6-((6-fluoropyridin-3-yl)methoxy)nicotinaldehyde.

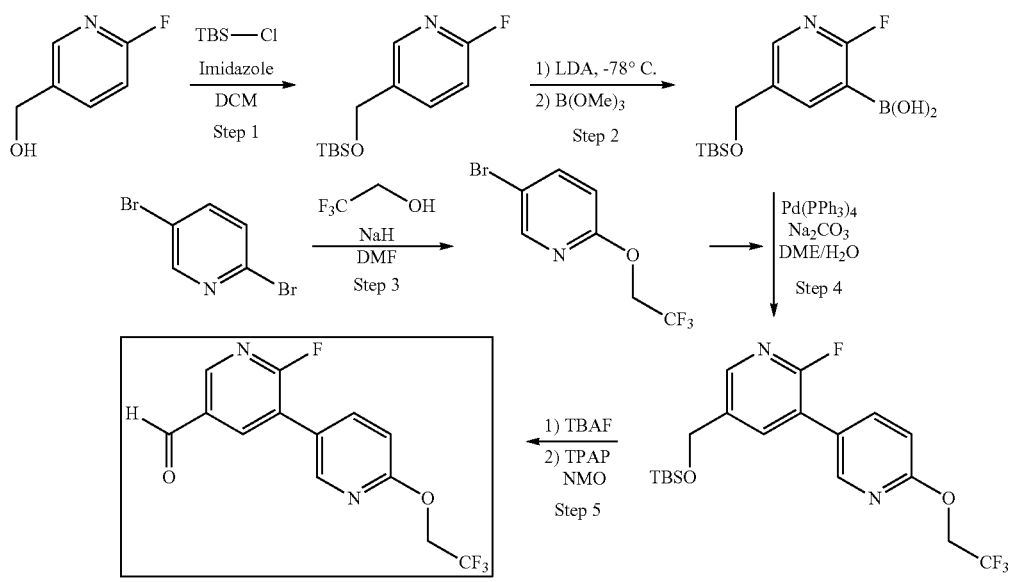

Preparation of 6-fluoro-5-(6-(2,2,2-trifluoroethoxy)pyridin-3-yl)nicotinaldehyde Step 1. (6-Fluoropyridin-3-yl)methanol (9.54 g, 75.0 mmol) and imidazole (5.11 g, 75.0 mmol) were placed into a round-bottomed flask with CH$_2$Cl$_2$ (300 mL). tert-butyldimethylsilyl chloride (10.9 g, 72.8 mmol) was dissolved in CH$_2$Cl$_2$ (75 mL) and added drop-wise to the reaction mixture, which was then allowed to stir overnight at rt. The reaction was quenched by adding water (100 mL). The biphasic mixture was then separated and the aqueous layer was washed with CH$_2$Cl$_2$ (2×30 mL). The combined organic layer was then washed with H$_2$O (3×50 mL), brine (50 mL), dried over MgSO$_4$, filtered, and concentrated to give 5-((tert-butyldimethylsilyloxy)methyl)-2-fluoropyridine as a yellow oil, which was used in the next step without further purification.

Step 2. Into a flame-dried 3-neck round-bottomed flask, was placed THF (300 mL). This was cooled to −78° C. while lithium diisopropyl amide (2 M solution, 36.3 mL, 72.5 mmol) was added. Once the desired temperature was achieved, 5-((tert-butyldimethylsilyloxy)methyl)-2-fluoropyridine (15.9 g, 65.9 mmol) in 30 mL of THF was added drop-wise through an addition funnel over ~30 min. The reaction mixture was then allowed to stir at −78° C. for 4 h. After the allotted time, the reaction was quenched by adding (MeO)$_3$B at −78° C. The reaction turned a yellow-orange color. At this point the reaction was warmed to rt and stirred additional 3 h. The mixture was then pH adjusted to 2.5 by adding 5N HCl. Once at pH 2.5, the THF was removed by rotary evaporation. Then the mixture was extracted with EtOAc (2×25 mL). Then the organic layer was washed with brine (1×30 mL), dried over MgSO$_4$, filtered, and concentrated to dryness. 5-((tert-butyldimethylsilyloxy)methyl)-2-fluoropyridin-3-ylboronic acid was obtained as a golden yellow solid. This material was used without further purification.

Step 3. 2,2,2-Trifluoroethanol (6.15 mL, 84.4 mmol) was placed into a flask with DMF (141 mL). To the reaction mixture was added NaH (3.4 g, 84.4 mmol) in portions. The reaction was then stirred for 30 min at 25° C. At this point, 2,5-dibromopyridine was added and the mixture was heated to 90° C. and stirred at that temperature overnight. The reaction was cooled to rt and diluted with EtOAc (100 mL). The organic layer was washed with H$_2$O (3×150 mL), brine (2×100 mL), dried (MgSO$_4$), filtered, and concentrated. This material was purified by column chromatography (15:1 hexane:EtOAc) to give 5-bromo-2-(2,2,2-trifluoroethoxy)pyridine as an oil.

Step 4. 5-((tert-Butyldimethylsilyloxy)methyl)-2-fluoropyridin-3-ylboronic acid (0.400 g, 1.40 mmol) was placed into a flask with a mixture of DME/H$_2$O (6 mL/2 mL). To the reaction mixture was added 5-bromo-2-(2,2,2-trifluoroethoxy)pyridine (0.358 g, 1.40 mmol), Na$_2$CO$_3$ (1.87 g, 17.6 mmol), and Pd(PPh$_3$)$_4$ (0.081 g, 0.07 mmol) and the reaction was allowed to stir at 80° C. overnight. The reaction was cooled to rt and concentrated. A solution of saturated NaHCO$_3$ (5 mL) was added, and then this mixture was extracted with EtOAc (3×20 mL). The combined organic layer was then washed with saturated NaHCO$_3$ (1×10 mL), brine (1×10 mL), dried (MgSO$_4$), filtered, and concentrated. Purification by column chromatography (9:1 hexane:EtOAc) gave 5-((tert-butyldimethylsilyloxy)methyl)-2-fluoro-3-(6-(2,2,2-trifluoroethoxy)pyridin-3-yl)pyridine.

Step 5. 5-((tert-Butyldimethylsilyloxy)methyl)-2-fluoro-3-(6-(2,2,2-trifluoroethoxy)pyridin-3-yl)pyridine (0.204 g, 0.490 mmol) was placed into a flask with 5.0 mL of tetrabutylammonium fluoride in THF and stirred for 4 h. The reaction was then quenched by adding water (5 mL) and extracting with EtOAc (3×5 mL). The combined organic layers were then washed with brine (1×5 mL), dried (MgSO$_4$), filtered, and concentrated. The resulting crude oil (0.145 g, 0.480 mmol) was then placed into a flame-dried flask, and to the reaction mixture was added N-methylmorpholine N-oxide (0.169 g, 1.44 mmol), 4 Å molecular sieves (10 mg), and CH$_2$Cl$_2$ (1.0 mL). Tetrapropylammonium perruthenate (8.43 mg, 0.024 mmol) was then added, and the suspension was stirred at rt overnight. The reaction mixture was worked-up by filtering through Celite® and concentrating the filtrate to give 6-fluoro-5-(6-(2,2,2-trifluoroethoxy)pyridin-3-yl)nicotinaldehyde.

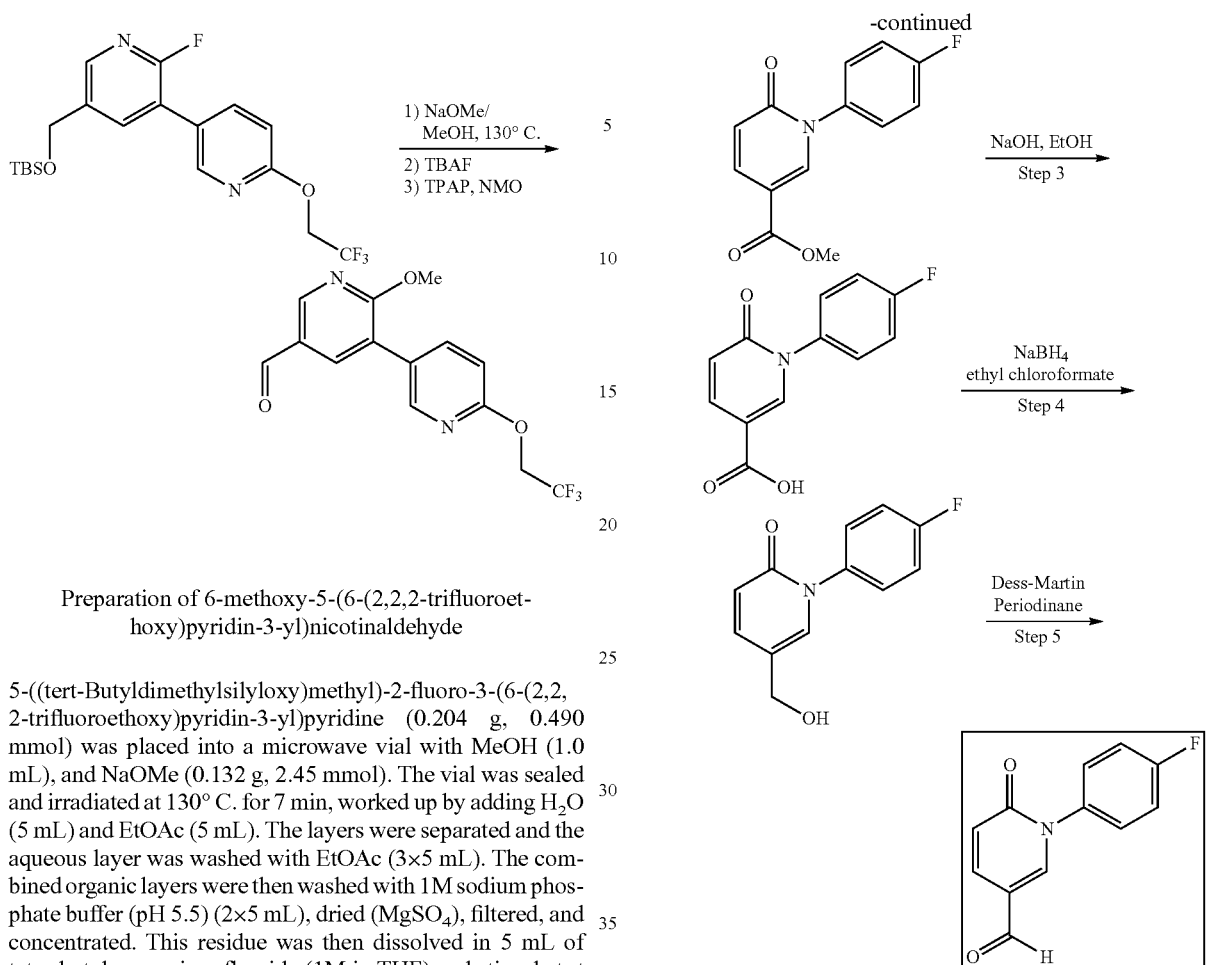

Preparation of 6-methoxy-5-(6-(2,2,2-trifluoroethoxy)pyridin-3-yl)nicotinaldehyde 5-((tert-Butyldimethylsilyloxy)methyl)-2-fluoro-3-(6-(2,2,2-trifluoroethoxy)pyridin-3-yl)pyridine (0.204 g, 0.490 mmol) was placed into a microwave vial with MeOH (1.0 mL), and NaOMe (0.132 g, 2.45 mmol). The vial was sealed and irradiated at 130° C. for 7 min, worked up by adding H$_2$O (5 mL) and EtOAc (5 mL). The layers were separated and the aqueous layer was washed with EtOAc (3×5 mL). The combined organic layers were then washed with 1M sodium phosphate buffer (pH 5.5) (2×5 mL), dried (MgSO$_4$), filtered, and concentrated. This residue was then dissolved in 5 mL of tetra-butylammonium fluoride (1M in THF) and stirred at rt overnight. The reaction was then quenched by adding water (5 mL) and extracting with EtOAc (3×5 mL). The combined organic layers were then washed with brine (1×5 mL), dried (MgSO$_4$), filtered, and concentrated. The resulting crude oil was then placed into a flame dried flask and to this was added N-methylmorpholine N-oxide (0.169 g, 1.44 mmol), 4 Å molecular sieves (10 mg), and CH$_2$Cl$_2$ (1.0 mL). Tetrapropylammonium perruthenate (8.43 mg, 0.024 mmol) was then added, and the suspension was stirred at rt overnight. The reaction mixture was then worked up by filtering through Celite® and concentrating the filtrate to give the title compound.

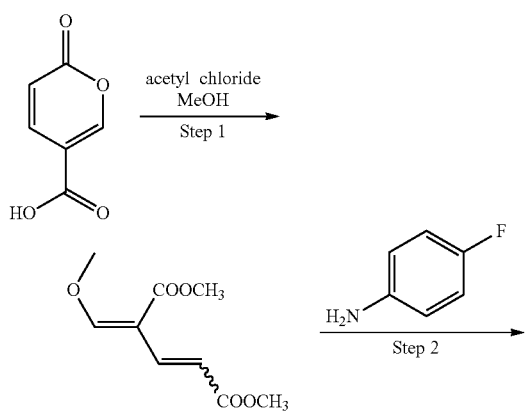

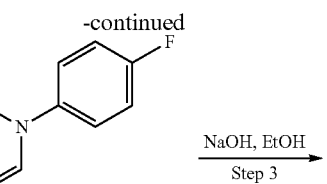

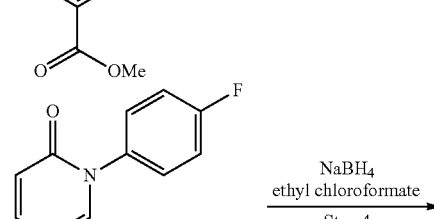

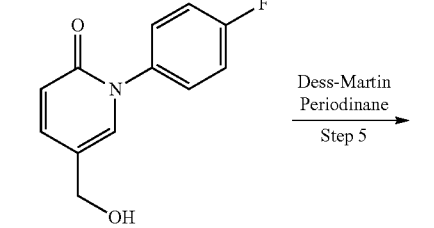

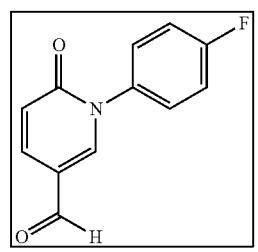

Preparation of 1-(4-fluorophenyl)-6-oxo-1,6-dihydro-3-pyridinecarbaldehyde

Step 1. A 500 mL round-bottomed flask was charged with 100 mL of MeOH, 6-oxo-6H-pyran-3-carboxylic acid (10 g, 71 mmol), and acetyl chloride (5.1 mL, 71 mmol). This mixture was heated to reflux for 12 h. After cooling to rt, the mixture was concentrated and the residue was dissolved in EtOAc (200 mL). The organics were washed with brine, dried with MgSO$_4$, filtered, and concentrated to give an oil. Purification by MPLC gave (2E,4Z)-dimethyl 4-(methoxymethylene)pent-2-enedioate as a mixture of isomers (~9:1 by $^1$H NMR) as a yellow solid.

Step 2. A 250 mL round-bottomed flask was charged with (Z)-dimethyl 4-(methoxymethylene)pent-2-enedioate (2.70 g, 13.5 mmol) and 50 mL of DMF. 4-fluorobenzenamine (1.43 ml, 14.8 mmol) was added dropwise at rt. After stirring at rt for 15 min, the yellow mixture was heated to reflux overnight. The reaction was then diluted with water (200 mL) and extracted with ether (3×100 mL). The combined extracts were dried with MgSO$_4$ and concentrated to give a solid. Purification by MPLC gave methyl 1-(4-fluorophenyl)-6-oxo-1,6-dihydropyridine-3-carboxylate as a slightly yellow solid.

Step 3. A 100 mL round-bottomed flask was charged with methyl 1-(4-fluorophenyl)-6-oxo-1,6-dihydropyridine-3-carboxylate (2.3 g, 9.1 mmol) and 20 mL of EtOH. To this was added NaOH (1.10 g, 27.0 mmol). This solution was stirred at rt for 20 h then concentrated. The mixture was acidified to pH 1 with conc HCl. The resulting precipitate was filtered and dried to give 1-(4-fluorophenyl)-6-oxo-1,6-dihydropyridine-3-carboxylic acid as an off-white solid.

Step 4. A 100 mL round-bottomed flask was charged with 1-(4-fluorophenyl)-6-oxo-1,6-dihydropyridine-3-carboxylic acid (1.8 g, 7.7 mmol) and 20 mL of THF. After cooling to −10° C., NEt$_3$ (1.2 mL, 8.9 mmol) and ethyl chloroformate (0.84 mL, 8.5 mmol) were added. This mixture was stirred at that temp for 45 min, then an aq soln of NaBH$_4$ (0.58 g, 15 mmol, in 10 mL of water) was added. After stirring for 3 h at −10° C., an additional 2 equiv of NaBH$_4$ (solid) were added. The reaction was quenched with aq 1N HCl (50 mL) and extracted with CH$_2$Cl$_2$ (3×75 mL). The residue was purified by MPLC to give 1-(4-fluorophenyl)-5-(hydroxymethyl)pyridin-2(1H)-one.

Step 5. A 100 mL round-bottomed flask was charged with 1-(4-fluorophenyl)-5-(hydroxymethyl)pyridin-2(1H)-one (0.420 g, 1.92 mmol) and 15 mL of CH$_2$Cl$_2$. To this was added Dess-Martin Periodinane (1.02 g, 2.39 mmol). After stirring at rt for 30 min, 15 mL of satd aq sodiumthiosulfate soln and 15 mL of satd aq sodium bicarbonate soln were added. The mixture was extracted with CH$_2$Cl$_2$ (3×30 mL) and the combined extracts were dried and concentrated. The residue was purified by MPLC to give 1-(4-fluorophenyl)-6-oxo-1,6-dihydro-3-pyridinecarbaldehyde.

Preparation of 6-(bromomethyl)-3-methoxy-2-(4-(trifluoromethyl)phenyl)pyridine

Step 1. To a solution of 2-iodo-6-methylpyridin-3-ol (0.97 g, 4.1 mmol) in THF (10 mL) at rt was added (trimethylsilyl)diazomethane (10 mL of a 2 M in Et$_2$O, 20 mmol). The reaction mixture was stirred at rt for 13 h and additional (trimethylsilyl)diazomethane solution (5 mL) was added. The reaction was heated to 35° C. for 3 h, quenched with acetic acid, and concentrated. The product 2-iodo-3-methoxy-6-methylpyridine was used without further purification in the next step.

Step 2. To a mixture of 4-(trifluoromethyl)phenylboronic acid (0.97 g, 5.1 mmol), S—PHOS (0.20 g, 0.47 mmol), potassium carbonate (2.0 g, 15 mmol), and Pd(OAc)$_2$ (0.061 g, 0.27 mmol) was added a solution of 2-iodo-3-methoxy-6-methylpyridine (prepared in the previous step) in acetonitrile (6 mL) followed by water (4 mL). The reaction mixture was degassed by bubbling nitrogen through the solution for 10 min, and the reaction mixture was heated to 75° C. After 4 h, the reaction mixture was diluted with EtOAc, washed with saturated NaHCO$_3$ (1×), brine (1×), dried over MgSO$_4$, filtered, and concentrated. Purification by flash column chromatography on silica gel (5% to 20% EtOAc in hexanes) gave 3-methoxy-6-methyl-2-(4-(trifluoromethyl)phenyl)pyridine.

Step 3. To a solution of 3-methoxy-6-methyl-2-(4-(trifluoromethyl)phenyl)pyridine (0.59 g, 2.2 mmol) in CCl$_4$ (40 mL) was added NBS (440 mg, 2.5 mmol) and AIBN (33 mg, 0.20 mmol). The reaction mixture was heated to reflux for 13 h, diluted with EtOAc, washed with water (1×), brine (1×), dried over MgSO$_4$, filtered through a pad (1.5 cm) of silica, and concentrated. The product 6-(bromomethyl)-3-methoxy-2-(4-(trifluoromethyl)phenyl)pyridine was used without further purification.

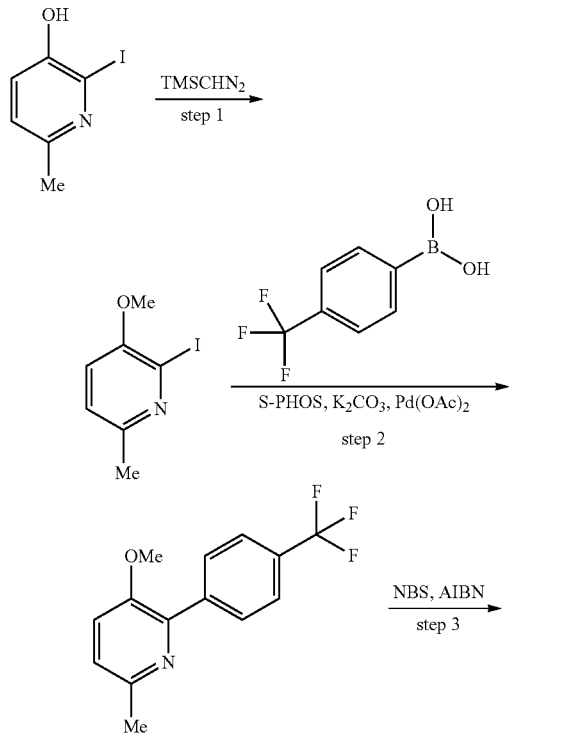

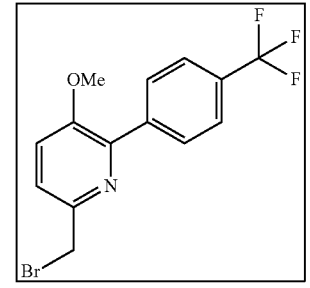

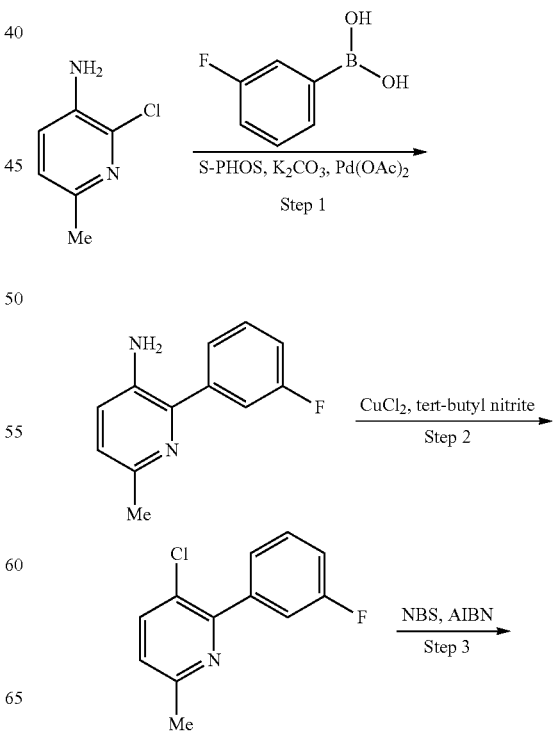

-continued

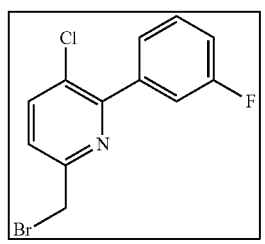

Preparation of 6-(bromomethyl)-3-chloro-2-(3-fluorophenyl)pyridine

Step 1. To a mixture of 3-fluorophenylboronic acid (1.6 g, 12 mmol), S—PHOS (0.304 g, 0.74 mmol), potassium carbonate (3.41 g, 25 mmol), 2-chloro-6-methylpyridin-3-amine 16 (1.3 g, 9.1 mmol), and Pd(OAc)$_2$ (0.085 g, 0.38 mmol) was added acetonitrile (14 mL) and water (9 mL). The reaction mixture was degassed by bubbling nitrogen through the solution for 10 min and the reaction mixture was heated to 78° C. After 4 h, the reaction mixture was diluted with EtOAc, washed with brine (1×), dried over MgSO$_4$, filtered, and concentrated. Purification by flash column chromatography on silica gel (10% to 50% EtOAc in hexanes) gave 2-(3-fluorophenyl)-6-methylpyridin-3-amine.

Step 2. To a suspension of copper(II) chloride (1.02 g, 7.58 mmol) in CH$_3$CN (15 mL) was added tert-butyl nitrite (1.30 mL, 10.9 mmol). The reaction mixture was heated to 65° C. and a solution of 2-(3-fluorophenyl)-6-methylpyridin-3-amine (1.33 g, 6.56 mmol) in CH$_3$CN (15 mL) was added via syringe. The reaction mixture was stirred for 20 min, diluted with EtOAc, washed with water (1×), brine (1×), dried over MgSO$_4$, filtered, and concentrated. Purification by flash column chromatography on silica gel (10% to 30% EtOAc in hexanes) gave 3-chloro-2-(3-fluorophenyl)-6-methylpyridine.

Step 3. To a solution of 3-chloro-2-(3-fluorophenyl)-6-methylpyridine (0.435 g, 2.0 mmol) in CCl$_4$ (40 mL) was added N-bromosuccinimide (0.350 g, 2.0 mmol). The reaction mixture was heated to 74° C. and AIBN (0.027 g, 0.16 mmol) was added. The reaction mixture was heated to reflux for 1 d, diluted with EtOAc, washed with H$_2$O (1×), brine (1×), dried over MgSO$_4$, filtered through a pad of silica (1.5 cm), and concentrated. The product, 6-(bromomethyl)-3-chloro-2-(3-fluorophenyl)pyridine, was used without further purification.

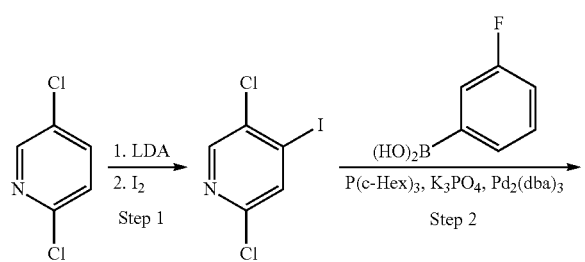

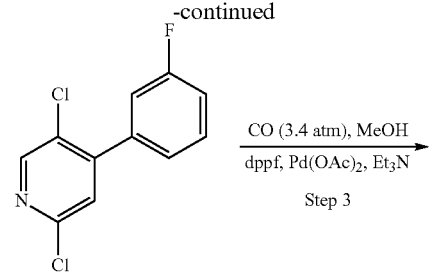

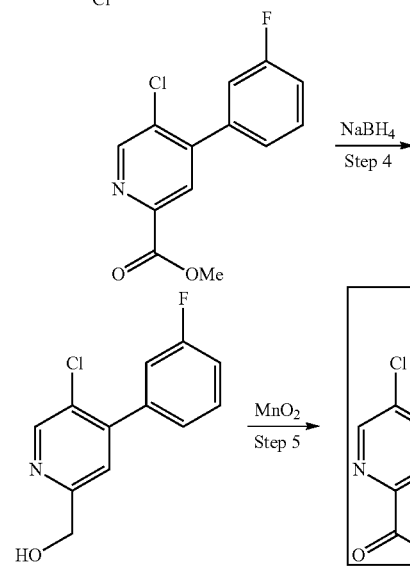

Preparation of 5-chloro-4-(3-fluorophenyl)picolinaldehyde

Step 1. To a solution of LDA (11 mL of a 2 M in heptane/THF/ethylbenzene, 22 mmol) in THF (30 mL) at −78° C. was added a solution 2,5-dichloropyridine (3.3 g, 22 mmol) in THF (20 mL) at −78° C. The reaction mixture was stirred at −78° C. for 1 h, and a solution of iodine (5.6 g, 22 mmol) in THF (20 mL) was added. The reaction mixture was stirred for 15 min, quenched with water, and warmed to rt. The reaction mixture was diluted with EtOAc, washed with water (1×), saturated Na$_2$S$_2$O$_3$ (1×), brine (1×), dried over MgSO$_4$, filtered, and concentrated. The crude reaction mixture was dissolved in dichloromethane (~50 mL), diluted with hexanes (~100 mL), and concentrated to a volume of ~100 mL. The solid was collected by filtration, and washed with hexanes to give 2,5-dichloro-4-iodopyridine.

Step 2. To a mixture of 3-fluorophenylboronic acid (0.776 g, 5.5 mmol), tris(dibenzylideneacetone)dipalladium(0) (0.140 g, 0.15 mmol), tricyclohexylphosphine (0.087 g, 0.31 mmol), and 2,5-dichloro-4-iodopyridine 20 (1.5 g, 5.6 mmol) was added dioxane (15 mL) and a solution of potassium phosphate (2.0 g, 9.6 mmol) in water (7.5 mL). The reaction mixture was degassed by bubbling nitrogen through the solution for 10 min, and the reaction mixture was heated to 95° C. After 2 h, the reaction mixture was diluted with EtOAc, washed with water (1×), brine (1×), dried over MgSO$_4$, filtered through a pad of silica gel (1.5 cm), and concentrated. Purification by flash column chromatography on silica gel (5% to 10% EtOAc in hexanes) gave 2,5-dichloro-4-(3-fluorophenyl)pyridine.

Step 3. To a mixture of 2,5-dichloro-4-(3-fluorophenyl)pyridine (0.604 g, 2.5 mmol), 1,1'-bis(diphenylphosphino)

ferrocene (dppf) (0.105 g, 0.19 mmol), and Pd(OAc)$_2$ (0.025 g, 0.11 mmol) was added MeOH (3.5 mL) and triethylamine (0.365 mL, 2.6 mmol). The nitrogen atmosphere was replaced with carbon monoxide (3.4 atm) and the reaction mixture was heated to 100° C. in a sealed tube. After 17 h, the reaction mixture was diluted with EtOAc, washed with saturated NaHCO$_3$ (1×), brine (1×), dried over MgSO$_4$, filtered, and concentrated. Purification by flash column chromatography on silica gel (5% to 20% EtOAc in hexanes) gave methyl 5-chloro-4-(3-fluorophenyl)picolinate.

Step 4. To a solution of methyl 5-chloro-4-(3-fluorophenyl)picolinate (0.196 g, 0.738 mmol) in MeOH (6 mL) was added NaBH$_4$ (0.152 g, 4.02 mmol). The reaction mixture was stirred at rt for 10 min, and diluted with EtOAc and water. The aqueous phase was extracted with EtOAc (1×) and the combined organic extracts were washed with brine (1×), dried over MgSO$_4$, filtered, and concentrated. Purification by flash column chromatography on silica gel (10% to 60% EtOAc in hexanes) gave (5-chloro-4-(3-fluorophenyl)pyridin-2-yl)methanol.

Step 5. To a solution of (5-chloro-4-(3-fluorophenyl)pyridin-2-yl)methanol (0.138 g, 0.58 mmol) in dichloromethane (5 mL) at room temperature was added manganese dioxide (0.49 g, 5.6 mmol). The reaction mixture was stirred at room temperature for 3 d, filtered, and concentrated. Purification by flash column chromatography on silica gel (10% to 20% EtOAc in hexanes) gave 5-chloro-4-(3-fluorophenyl)picolinaldehyde.

Preparation of
9-ethyl-9H-β-carboline-3-carbaldehyde

Step 1. To a suspension of sodium hydride 60% dispersion in mineral oil (138 mg, 3.45 mmol, 1.1 eq) in anhydrous N,N-dimethylformamide (10 mL) was added dropwise at 0° C. and under nitrogen a solution of ethyl pyrido[3,4]indole-3-carboxylate (765 mg, 3.18 mmol, 1 eq) in anhydrous N,N-dimethylformamide (10 mL). The suspension was stirred at 0° C. for 45 min and iodoethane (596 mg, 3.82 mmol, 1.5 eq) was added at 0° C. The reaction was then stirred at rt for 16 h. The mixture was quenched with water and extracted with ethyl acetate. The organic layer was dried (MgSO$_4$), filtered, and concentrated under reduced pressure. The residue was partitioned between hexane and acetonitrile. The acetonitrile layer was collected and concentrated under reduced pressure. The crude product was dissolved in ethyl acetate and washed with water to remove any residual N,N-dimethylformamide and provide the title compound as a yellow oil. Mass Spec. m/z=269 [M+H$^+$].

Step 2. To a suspension of lithium aluminium hydride (116 mg, 3.06 mmol, 1 eq) in anhydrous tetrahydrofuran (15 mL) was added at 0° C. under nitrogen a solution of 9-ethyl-9H-β-carboline-3-carboxylic acid ethyl ester (820 mg, 3.06 mmol, 1 eq) in anhydrous tetrahydrofuran (25 mL). The reaction mixture was stirred at 0° C. for 6 h then quenched with a 5% aqueous solution of sodium hydroxide (2.88 mL). The solid formed was filtered, washed with ethyl acetate and dried to afford the title compound, which is used without further purification. Mass Spec m/z=227 [M+H$^+$].

Step 3. To a solution of (9-ethyl-9H-β-carbolin-3-yl)-methanol (560 mg, 2.47 mmol, 1 eq) in acetone (20 mL) was added manganese (IV) oxide (2.942 g, 33.84 mmol, 14 eq). The solution was stirred at rt. After 3 d, as only 50% conversion is observed, more manganese (IV) oxide was added (229 mg, 2.63 mmol, 1.1 eq) and the mixture was heated to 50° C. for 2.5 d. After this time, the reaction was cooled down to rt, filtered through CELITE®, and the solid was washed with dichloromethane. The filtrates were combined and concentrated under reduced pressure. The residue was purified by column chromatography eluting with ethyl acetate to give the title compound as a yellow oil. Mass Spec m/z=225 [M+H+].

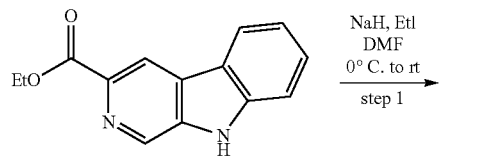

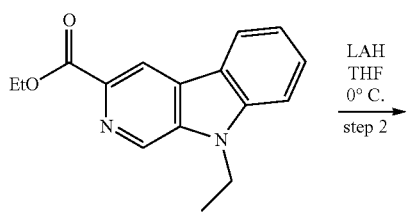

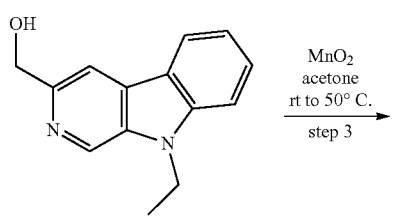

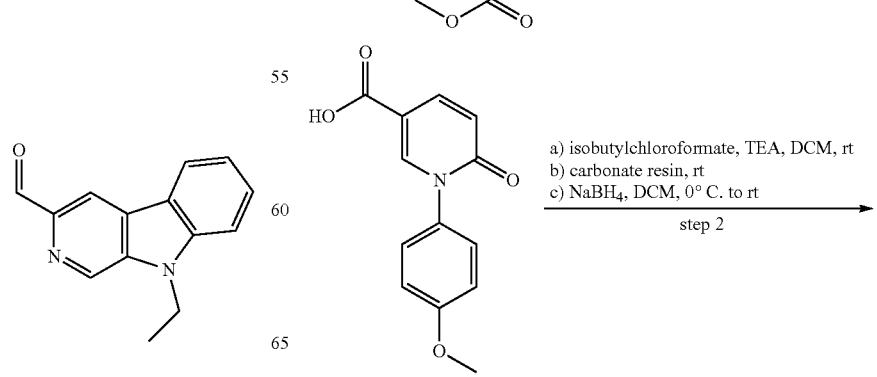

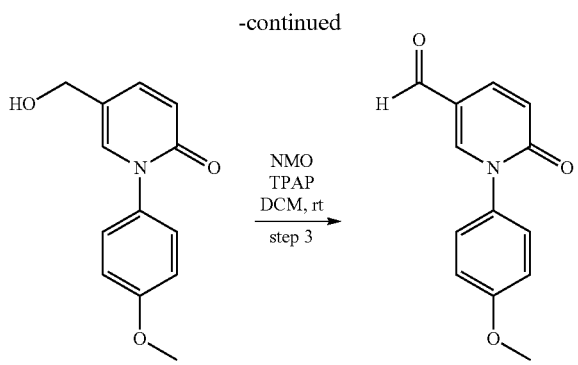

Preparation of 1-(4-methoxy-benzyl)-6-oxo-1,6-dihydro-pyridine-3-carbaldehyde

Step 1. To a solution of methyl coumalate (1 g, 6.49 mmol, 1 eq) in ethanol (30 mL) was added p-anisidine (0.79 g, 6.49 mmol, 1 eq). The reaction mixture was heated to reflux for 16 h. After this time, the solvent was removed under reduced pressure, and the residue was purified by column chromatography eluting with 3:2 ethyl acetate/hexane to afford 1-(4-methoxy-benzyl)-6-oxo-1,6-dihydro-pyridine-3-carboxylic acid methyl ester. Mass Spec m/z=260 [M+H$^+$]. To a solution of 1-(4-methoxy-benzyl)-6-oxo-1,6-dihydro-pyridine-3-carboxylic acid methyl ester (400 mg, 1.54 mmol, 1 eq) in 3:1 tetrahydrofuran/methanol (20 mL) was added lithium hydroxide (148 mg, 6.17 mmol, 4 eq). The mixture was stirred at rt for 48 h then heated to 50° C. for 16 h. After this time, the mixture was concentrated under reduced pressure and partitioned between water and ethyl acetate. The aqueous layer was acidified with a 2N aqueous solution of hydrochloric acid then extracted with ethyl acetate. The organic layers were combined and washed with water, dried (MgSO$_4$), filtered and concentrated under reduced pressure to afford 1-(4-methoxy-benzyl)-6-oxo-1,6-dihydro-pyridine-3-carboxylic acid, which is used without further purification.

Step 2: To a solution of crude 1-(4-methoxy-benzyl)-6-oxo-1,6-dihydro-pyridine-3-carboxylic acid (55.3 mg, 0.226 mmol, 1 eq) in anhydrous dichloromethane (10 mL) was added isobutyl chloroformate (29.6 µL, 30 mg, 0.226 mmol, 1 eq) and triethylamine (47 µL, 34 mg, 0.338 mmol, 1.5 eq). The mixture was stirred at rt for 4 h. Carbonate resin (3 mmol/g, 150 mg, 0.451 mmol, 2 eq) was added and the reaction is stirred for another 2 h. The mixture was then cooled down to 0° C. and sodium borohydride (25 mg, 0.677 mmol, 3 eq) was added and the mixture stirred at rt for 16 h. After this time, the reaction was filtered, and the filtrate was diluted with dichloromethane then washed with water and brine. The organic layer was dried (MgSO$_4$), filtered, and concentrated under reduced pressure. The residue was purified by column chromatography eluting with 95:5 dichloromethane/methanol to give 5-hydroxymethyl-1-(4-methoxy-benzyl)-1H-pyridin-2-one. Mass Spec m/z=232 [M+H$^+$].

Step 3. To a solution of 5-hydroxymethyl-1-(4-methoxy-benzyl)-1H-pyridin-2-one (35 mg, 151.5 µmol, 1 eq), 4-methyl morpholine N-oxide (26.7 mg, 227.2 µmol, 1.5 eq) and powdered 4 Å molecular sieves in dichloromethane (10 mL) was added in one portion tetrapropylammonium perruthenate (2.7 mg, 7.5 µmol, 0.05 eq). The reaction was stirred at rt for 2 h. After this time, the mixture was filtered through silica and the silica plug was washed with 95:5 dichloromethane/methanol. The filtrates were combined and concentrated under reduced pressure. The residue was purified by column chromatography eluting with 2:1 ethyl acetate/hexane to give 1-(4-methoxy-benzyl)-6-oxo-1,6-dihydro-pyridine-3-carbaldehyde. Mass Spec. m/z=230 [M+H$^+$].

The detailed schemes of synthesis of the compounds of the invention are described in detail in Examples below.

B. Pharmaceutical Compositions and Administration

Compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methansulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al. *J. Pharm. Sci.* 66: 1, 1977. In certain embodiments of the invention salts of hydrochloride and salts of methanesulfonic acid can be used.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the calcium receptor-active compound in the compositions useful in the invention can range from about 0.1 mg to about 180 mg, for example from about 5 mg to about 180 mg, or from about 1 mg to about 100 mg of the calcimimetic compound per subject. In some aspects, the therapeutically effective amount of calcium receptor-active compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a calcium receptor-active compound to a subject alone, the compound administered will normally be present as an active ingredient in a pharmaceutical composition. Thus, a pharmaceutical composition of the invention may comprise a therapeutically effective amount of at least one calcimimetic compound, or an effective dosage amount of at least one calcimimetic compound.

As used herein, an "effective dosage amount" is an amount that provides a therapeutically effective amount of the calcium receptor-active compound when provided as a single dose, in multiple doses, or as a partial dose. Thus, an effective dosage amount of the calcium receptor-active compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the calcimimetic compound is administered by administering a portion of the composition.

Alternatively, a pharmaceutical composition in which two or more unit dosages, such as in tablets, capsules and the like, are required to administer an effective amount of the calcium receptor-active compound may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

III. Therapeutic Uses of the Compounds of the Invention

Compounds and compositions of the present application which act on calcium receptors may thus be used, in one aspect, for the treatment or prevention of diseases or disorders linked with abnormal physiological behaviour of calcium receptors such as membrane calcium receptors capable of binding extracellular calcium.

A patient in need of the treatment, as used herein, is a human having a disease or disorder characterized by one or more of the following: (1) abnormal calcium ion homeostasis, (b) an abnormal level of a messenger whose production or secretion is affected by the calcium sensing receptor (CaSR) activity, or (3) an abnormal level of activity of a messenger whose function is affected by the calcium sensing receptor activity. In one aspect, the patient has a disease or disorder characterized by an abnormal level of one or more calcium sensing receptor-regulated components and the compound is active on a CaSR of a cell including parathyroid cell, bone osteoclast, juxtaglomerular kidney cell, kidney messengial cell, glomerular kidney cell, proximal tubule kidney cell, distal tubule kidney cell, cell of the thick ascending limb of Henle's loop and/or collecting duct, parafolliculr cell in the thyroid (C-cell), intestinal cell, platelet, vascular smooth muscle cell, GI tract cell, pituitary cell, or hypothalamic cell.

Diseases characterized by abnormal calcium homeostasis include hyperparathyroidism and the like (as described, e.g., in standard medical textbooks, such as "Harrison's Principles of Internal Medicine". The compounds and compositions of the present invention can be used, in particular, to participate in a reduction of the serum levels in the parathyroid hormone known as PTH: these products could thus be useful, in one aspect, for the treatment of diseases such as hyperparathyroidism. Similarly, abnormalities in calcium homeostasis, such as hypercalcaemia, can be treated with these compounds. Further, the compounds of the invention can treat hyperplasia and parathyroid adenoma. In another aspect, the compounds of the invention can have properties which enable them to reduce bone resorption which depends directly on the fluctuation of circulating PTH levels: these products could be useful, in particular, for the treatment of diseases such as osteoporosis, osteopaenia Paget's disease and the reconstruction of fractures. They can also be used in the treatment and prophylaxis of polyarthritis and osteoarthritis.

In one aspect, the invention provides a method of inhibiting, decreasing or preventing vascular calcification in an individual. The method comprises administering to the individual a therapeutically effective amount of the calcimimetic compound of the invention. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits.

In one aspect, the compounds of the invention may be used to prevent or treat atherosclerotic calcification and medial calcification and other conditions characterized by vascular calcification. In one aspect, vascular calcification may be associated with chronic renal insufficiency or end-stage renal disease. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

In one aspect, administration of an effective amount of the compounds of the invention can reduce serum PTH without causing aortic calcification. In another aspect, administration of the compounds of the invention can reduce serum creatinine level or can prevent increase of serum creatinine level. In another aspect, administration of the compounds of the invention can attenuates parathyroid (PT) hyperplasia.

The compounds of the invention may be administered alone or in combination with other drugs for treating vascular calcification, such as vitamin D sterols and/or RENAGEL®. Vitamin D sterols can include calcitriol, alfacalcidol, doxercalciferol, maxacalcitol or paricalcitol. In one aspect, the compounds of the invention can be administered before or after administration of vitamin D sterols. In another aspect, the compounds of the invention can be co-administered with vitamin D sterols. The methods of the invention can be practiced to attenuate the mineralizing effect of calcitriol on vascular tissue. In one aspect, the methods of the invention can be used to reverse the effect of calcitriol of increasing the serum levels of calcium, phosphorus and CaxP product thereby preventing or inhibiting vascular calcification. In another aspect, the compounds of the invention of the invention can be used to stabilize or decrease serum creatinine levels. In one aspect, in addition to creatinine level increase due to a disease, a further increase in creatinine level can be due to treatment with vitamin D sterols such as calcitriol. In addition, the compounds of the invention may be administered in conjunction with surgical and non-surgical treatments. In one aspect, the methods of the invention can be practiced in injunction with dialysis.

In one aspect, the compounds of the invention can be used for treating abnormal intestinal motilities disorders such as diarrhea. The methods of the invention comprise administering to the individual a therapeutically effective amount of the compounds of Formula I.

As used herein, the term "diarrhea" refers to a condition of three or more unformed stools in a 24-hour period of volume more than 200 g per day. In one aspect, diarrhea can be osmotic, i.e., resulting if the osmotic pressure of intestinal contents is higher than that of the serum. This condition may result from malabsorption of fat (e.g., in celiac disease) or of lactose (e.g., in intestinal lactase deficiency), or it can happen due to the use of certain laxatives (e.g., lactulose, magnesium hydroxide) or artificial sweeteners (e.g., sorbitol, mannitol). In another aspect, diarrhea can be secretory, i.e., occurring when there is a net secretion of water into the lumen. This may occur with bacterial toxins (such as those produced, e.g., by *E. coli* and *Vibrio cholerae*), or with hormones, such as vasoactive intestinal polypeptide, which is produced by rare islet cell tumors (pancreatic cholera). Both osmotic and secretory diarrheas result from abnormalities in the small intestine such that the flow of water through the ileocecal area overcomes the absorptive capacity of the colon.

In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with chemotherapy, radiation treatment, inflammation or toxic traumatic injury. In another aspect, exudative diarrhea can be associated with a gastrointestinal or abdominal surgery.

In another aspect, diarrhea can be due to acceleration of intestinal transit (rapid transit diarrhea). Such condition may occur because the rapid flow-through impairs the ability of the gut to absorb water.

In one aspect, the invention provides the compounds and compositions for treating abnormal gastric fluid secretion/absorption disorders in conjunction with treating underlying causes of, for example, diarrhea or with other treatment methods. In one aspect, calcimimetics can be administered to a subject before, after or concurrently with oral rehydration therapy. For example, oral rehydration therapy may contain the following ingredients: sodium, potassium, chloride, bicarbonate, citrate and glucose. In another aspect, the compounds of the invention can be administered to a subject before, after or concurrently with an antimotility agent, such as loperamide (Imodium), diphenoxylate, or bismuth subsalicylate (Pepto-Bismol). In another aspect, calcimimetics can be administered with antibiotics (e.g., trimethoprim-sulfamethoxazole (Bactrim DS), ciprofloxacin (Cipro), norfloxacin (Noroxin), ofloxacin (Floxin), doxycycline (Vibramycin), erythromycin). In one aspect, the compounds of the invention can be administered together with calcium or polyamines such as spermine, spermidine, putrescine, and ornithine metabolites or amino acids such of L-tryptophan, L-phenylalanine. In another aspect, the compounds of the invention can be administered together with sodium and glucose. In addition, the compounds of the invention may be administered in conjunction with surgical and non-surgical treatments.

The invention further provides methods for modulating intestinal fluid secretion and absorption. In one aspect, the purpose can be to increase fluid absorption and/or decrease fluid secretion in a subject and thus the methods of the invention can comprise administering an effective amount of a pharmaceutical composition comprising a compound of the invention.

The invention provides methods of modulation the absorption or secretion of a drug, poison or nutrient in the intestinal tract of a subject, comprising administering an effective amount of a pharmaceutical composition comprising a compound of the invention together with a pharmaceutically acceptable carrier to the subject. In one aspect, the invention provides methods of treatment of a malassimilation or a malabsorption of a subject, comprising administering an effective amount of a pharmaceutical composition comprising a compound of Formula I together with a pharmaceutically acceptable carrier to the subject.

As used herein, the term "malassimilation" encompasses impaired processes of food digestions and absorption occurring in one of two ways (1) through intraluminal disorders (maldigestion of food) and (2) through intramural disorders (malabsorption of food).

Methods of the invention comprising administering a pharmaceutical composition of the invention can also be practiced to treat malnutrition in a subject. For example, a subject can be malnourished if the subject is grossly underweight (weight for height is below 80% of the standard), grossly overweight (weight for height above 120% of the standard), if the subject unintentionally lost 10% or more of body weight, has a gastrointestinal tract surgery, experienced nutrient losses (e.g., from diarrhea, dialysis, vomiting), has increased metabolic needs (e.g., due to pregnancy, lactation, increased physical activity, fever, injury), is an alcoholic or chronic drug user (antibiotics, antidepressants, diuretics), has medical conditions which interfere with nutrient intake, absorption, metabolism, or utilization, has poor dentition (particularly in the elderly subjects), or has mouth sores due to herpes, HIV or chemotherapy. In another aspect, the subject can be malnourished due to dietary risk factors (e.g., loss of appetite, inadequate food or nutrient intake, lack of variety of foods, fad, weight-loss diets, inadequate fiber, excessive fat, sodium, sugar, excess alcohol, eats too few fruits, vegetables) or due to social risk factors (e.g., chronic ill health, poverty, inadequate money to buy food, low socioeconomic status, immobility or inability to purchase, store, or cook food, social isolation, eats alone most of the time, substance abuser, conditions which limit subject's ability to eat). Further, the methods of the invention can be practiced when a subject has limited access to nutrients such as during survival following environmental disasters, survival at sea, marooning and deep-sea living or space travel.

In one aspect, the podocyte diseases or disorders treated by methods of the present invention stem from the perturbations in one or more functions of podocytes. These functions of podocytes include: (i) a size barrier to protein; (ii) charge barrier to protein; (iii) maintenance of the capillary loop shape; (iv) counteracting the intraglomerular pressure; (v) synthesis and maintenance of the glomerular basement membrane (GMB); (iv) production and secretion of vascular endothelial growth factor (VEGF) required for the glomerular endothelial cell (GEN) integrity.

Such disorders or diseases include but are not limited to loss of podocytes (podocytopenia), podocyte mutation, an increase in foot process width, or a decrease in slit diaphragm length. In one aspect, the podocyte-related disease or disorder can be effacement or a diminution of podocyte density. In one aspect, the diminution of podocyte density could be due to a decrease in a podocyte number, for example, due to apoptosis, detachment, lack of proliferation, DNA damage or hypertrophy.

In one aspect, the podocyte-related disease or disorder can be due to a podocyte injury. In one aspect, the podocyte injury can be due to mechanical stress such as high blood pressure, hypertension, or ischemia, lack of oxygen supply, a toxic substance, an endocrinologic disorder, an infection, a contrast agent, a mechanical trauma, a cytotoxic agent (cis-platinum, adriamycin, puromycin), calcineurin inhibitors, an inflammation (e.g., due to an infection, a trauma, anoxia, obstruction, or ischemia), radiation, an infection (e.g., bacterial, fungal, or viral), a dysfunction of the immune system (e.g., an autoimmune disease, a systemic disease, or IgA nephropathy), a genetic disorder, a medication (e.g., anti-bacterial agent, anti-viral agent, anti-fungal agent, immunosuppressive agent, anti-inflammatory agent, analgestic or anticancer agent), an organ failure, an organ transplantation, or uropathy. In one aspect, ischemia can be sickle-cell anemia, thrombosis, transplantation, obstruction, shock or blood loss. In on aspect, the genetic disorders may include congenital nephritic syndrome of the Finnish type, the fetal membranous nephropathy or mutations in podocyte-specific proteins, such as α-actin-4, podocin and TRPC6.

In one aspect, the podocyte-related disease or disorder can be an abnormal expression or function of slit diaphragm proteins such as podocin, nephrin, CD2AP, cell membrane proteins such as TRPC6, and proteins involved in organization of the cytoskeleton such as synaptopodin, actin binding proteins, lamb-families and collagens. In another aspect, the podocyte-related disease or disorder can be related to a disturbance of the GBM, to a disturbance of the mesangial cell function, and to deposition of antigen-antibody complexes and anti-podocyte antibodies.

In one aspect, the podocyte-related disease or disorder can be proteinuria, such as microalbumiuria or macroalbumiuria. In another aspect, the podocyte-related disease or disorder can be tubular atrophy.

In one aspect, the present invention provides method of treatment or prevention of inflammatory bowel disease using the compounds of the invention. Inflammatory bowel disease, or IBD, as used herein, is a disease characterized by inflammation or ulcerations in the small and/or large intestine with chronically recurring symptoms of abdominal pain and alteration in bowel habits. IBD has been classified into the broad categories of Crohn's disease (CD) and ulcerative colitis (UC). In one aspect, the invention provides methods for treating UC using calcimimetic compounds and compositions. In another aspect, the methods of the invention can be used for treatment of CD using calcimimetic compounds and compositions. In one aspect, methods of the present invention result in prevention of onset or alleviation of one or more signs or symptoms of UC or CD. Table 1 further summarizes inflammatory markers in pathophysiology of IBD and signs/symptoms commonly found in ulcerative colitis and Crohn's disease.

TABLE 1

| Sign/Symptom | Ulcerative Colitis | Crohn's Disease |
|---|---|---|
| Area of intestinal tract affected | Any part of innermost lining of colon, continuous with no patches of normal tissues | Lower ileum most common but can flare up anywhere, including the colon, patches of normal tissue between affected areas; can affect entire intestinal wall |
| Diarrhea | Typically four episodes per day | Typically four episodes per day |
| Abdominal pain/cramping | Mild tenderness, lower abdominal cramping | Moderate to severe abdominal tenderness in right lower quadrant |
| Blood in stool | Present; amount depends on disease severity | May be present; amount depends on disease severity |
| Fatigue | Result of excessive blood loss and anemia | Result of excessive blood loss, anemia, and poor nutrient absorption |
| Fever | Low-grade in severe cases | Low-grade in severe cases |
| Physical examination | Rectal exam may show peri-anal irritation, fissures, hemorrhoids, fistulas, and abscesses | Peritoneal irritation, abdominal or pelvis mass |
| Weight loss/anorexia | Weight loss in more severe cases | Weight loss and anorexia common due to poor digestion and intestinal absorption |
| Appetite | Often decreased during periods of disease exacerbation | Often decreased during periods of disease exacerbation |
| Risk of colon cancer | Increased | Increased |

In one aspect, the present invention provides method of treatment or prevention of irritable bowel syndrome. Irritable bowel syndrome, or IBS, as used herein, is a gastrointestinal disorder characterized by altered bowel habits and abdominal pain, typically in the absence of detectable structural abnormalities or biochemical cause. The Rome II criteria can be used to diagnose IBS and rule out other disorders. The criteria include at least 3 months of the following continuous recurrent symptoms: abdominal pain or discomfort that is relieved by defecation or is associated with a change in the frequency or consistency of stool, and disturbed defecation involving two or more of the following characteristics at least 25% of the time: altered stool frequency, altered stool form (e.g., lumpy or hard, or loose or watery), altered stool passage (e.g., straining, urgency, or feeling of incomplete evacuation), passage of mucus, bloating or feeling of abdominal distention. The intensity and location of abdominal pain in IBS can be highly variable, even within an individual patient: it is localized to the hypogastrium in 25%, the right side in 20%, the left side in 20%, and the epigastrium in 10% of the patients. The pain can be generally crampy or achy, although sharp, dull, gas-like, or non-descript pains are also common. In one aspect, patients with IBS may present with constipation (IBS-C, constipation predominant IBS), diarrhea (IBS-D, diarrhea-predominant IBS), or constipation alternating with diarrhea (IBS-A, mixed symptom IBS, or "alternators"). Long period of straining may be required for fecal evaluation both in constipation- and diarrhea-predominant patient. Constipation may persist for weeks to months, interrupted by brief periods of diarrhea. Feelings of incomplete fecal evacuation may lead to multiple attempts at stool passage daily. In patients with IBS-D, stools are characteristically loose and frequent but of normal daily volume. Mucus discharge has been reported in up to 50% of patients with IBS. Upper gut symptoms are common in IBS, with 25% to 50% of patients reporting heartburn, early satiety, nausea, and vomiting, up to 87% note intermittent dyspepsia. Agreus L. et al. (1995) Gastroenterology 109: 671. Extraintestinal complaints in patients with IBS include chronic pelvic pain, fibromyalgia, genitourinary dysfunctions, such as dysmenorrheal, dyspareunia, impotence, urinary frequency, nocturia, and a sensation of incomplete bladder emptying. Impaired sexual function is reported by 83% of patients with IBS. Patients with functional bowel disorders have higher incidences of hypertension, headaches, peptic ulcer disease, rashes than the general population and more commonly report fatigue, loss of concentration, insomnia, palpitations, and unpleasant tastes in the mouth.

While the pathogenesis of IBS is poorly understood, it has been proposed that abnormal gut motor and sensory activity, central neural dysfunction, psychological disturbances, stress and luminal factors play a role. IBS has been associated with colonic and small intestinal motility abnormalities, as well as with motor abnormalities in other smooth muscle sites. The visceral sensory abnormalities, which may be responsible for sensations of pain, gas, or bloating in IBS, have been a major focus of investigation. Perception of abdominal symptoms is mediated by afferent neural pathways which are activated by visceral stimuli acting on chemoreceptors, mechanoreceptors, and receptors in the mesentery which may play a role in painful stimulation of the gut. Information from these activated receptors is carried in spinal afferent nerves and thus transmitted to the brain where conscious perception occurs. It is postulated that IBS results from sensitization of afferent pathways such that normal physiological gut stimuli not perceived by healthy individuals induce pain in the patient with IBS. The sensitizing event responsible for induction of symptoms in IBS is unknown. The clinical association of emotional disorders and stress with symptom exacerbation and the therapeutic response to therapies that act on cerebral cortical sites strongly suggests the role of central nervous system factors in the pathogenesis of IBS. However, it is unclear whether IBS represents a primary gut disturbance with inappropriate input from the central nervous system or a central nervous system disorder with centrally directed changes in gut motor and sensory activity. Further, both mental stress and administration of the cholinesterase inhibitor neostigmine evoke increases in colonic motility and changes in electroencephalographic waveforms which are exaggerated in patients with IBS compared to healthy volunteers, suggesting that both the gut and brain are hypersensitive in IBS. Investigations of the effects of stress reinforce the importance of the brain-gut axis in the regulation of colonic activities. A strongly positive relationship has been reported between daily stress and daily symptoms in women with IBS. Levy R. et al. (1997) J. Behav. Med. 20: 177.

The present invention, thus generally described, will be understood more readily by reference to the following examples, which are provided by way of illustration and are not intended to be limiting of the present invention. Compounds of the invention may be synthesized from simple starting molecules and commercially available materials as illustrated in Examples. Various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence. The structure of the prepared compounds is verified by mass spectral data. For some compounds, ions having mass greater than M+H are reported. These ions generally represent dimers or trimers of the synthesized compound, and in some instances represent trifluoroacetate adducts generated from the mobile phase of the LC/MS. The trifluoroacetate adducts will have a weight of M+115.

Methods A-G provide exemplary synthetic methods for the preparation of the compounds of the present invention. One of skill in the art will understand that additional methods are also useful. In other words, the compounds of the invention can be made using organic synthesis using starting materials, reagents and reactions well known in the art.

Certain compounds of the invention may be conveniently prepared by a general process outlined in Method A.

Method A

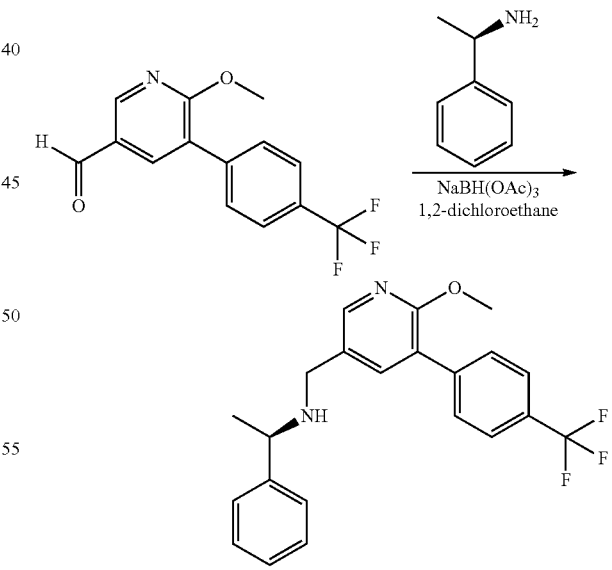

R-α-Methyl benzylamine (0.12 mL, 0.928 mmol) and 6-methoxy-5-(4-(trifluoromethyl)phenyl)-3-pyridinecarbaldehyde (0.261 g, 0.928 mmol) were dissolved in 3.0 mL of 1,2-dichloroethane in a 10 mL round bottom flask. The solution was allowed to stir at 25° C. for 1 h, at which point NaBH(OAc)$_3$ (0.295 g, 1.39 mmol) was added in one portion. The reaction was then stirred for 16 h at 25° C. The reaction was quenched by adding 5N NaOH (1.5 mL) and stirring vigorously for 30 min. The layers were separated and the aqueous layer was washed with DCM (3×2.0 mL). The combined organic layers were dried over MgSO$_4$, filtered, and concentrated to give crude product, which was then purified by silica gel chromatography (1:1 hexane-EtOAc) to afford (1R)—N-((6-methoxy-5-(4-(trifluoromethyl)phenyl)-3-pyridinyl)methyl)-1-phenylethanamine 1. MS m/z: 387 (MH$^+$).

Method B

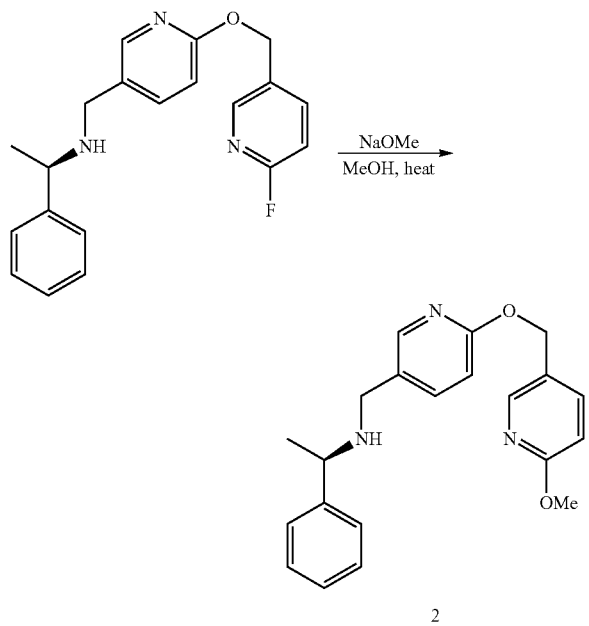

(1R)—N-((6-((6-Fluoro-3-pyridinyl)methoxy)-3-pyridinyl)methyl)-1-phenylethanamine (0.500 g, 1.48 mmol) was added to a microwave tube with NaOMe (0.400 g, 7.40 mmol) and MeOH (1.0 mL). The vial was sealed and irradiated for 7 min at 130° C. After the allotted time, the reaction was worked up by adding water (1.0 mL) and EtOAc (1.0 mL). The layers were separated and the aqueous layer was washed with EtOAc (3×1.0 mL). The combined organic layers were then washed with 1M sodium phosphate buffer (pH 5.5) (2×3.0 mL), dried over MgSO$_4$, filtered, and concentrated to leave an oil. This was then purified by silica gel chromatography (1:1 hexane-EtOAc) to afford (1R)—N-((6-((6-methoxy-3-pyridinyl)methoxy)-3-pyridinyl)methyl)-1-phenylethanamine 2. MS m/z: 350 (MH$^+$).

Method C

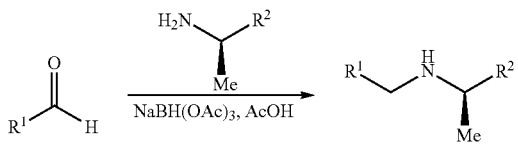

To a solution of aldehyde (1 equiv) and amine (1.1-1.3 equiv) in 1,2-dichloroethane at rt was added acetic acid (as much as 1 equiv) and sodium triacetoxyborohydride (1.2-2.5 equiv). The mixture was stirred overnight or until the reaction was complete by TLC. The reaction mixture was diluted with EtOAc or CH$_2$Cl$_2$, washed with saturated NaHCO$_3$ and, when EtOAc was used in the work-up, the organic layer was washed with brine. The organic layer was then dried over Na$_2$SO$_4$ or MgSO$_4$, filtered, and concentrated in vacuo. Purification by column chromatography on silica gel gave the desired product. In cases where starting amine was still present in the desired product, the product was heated in CH$_2$Cl$_2$ with aldehyde resin (4-benzyloxybenzaldehyde, polymer-bound) for 1.5 d at 50° C. After cooling to rt, the resin was poured onto a filter funnel and washed with methanol, CH$_2$Cl$_2$, and THF. The filtrate was then concentrated in vacuo to give the desired product. In some instances the final product was treated with an excess of 1M HCl in Et$_2$O and evaporated under reduced pressure to afford the HCl salt of the desired product. Alternatively, the HCl salt of the desired product was formed by stirring the product in CH$_2$Cl$_2$ with 12 N HCl for 2-3 h. The HCl salt was isolated after the mixture was concentrated in vacuo.

Method D

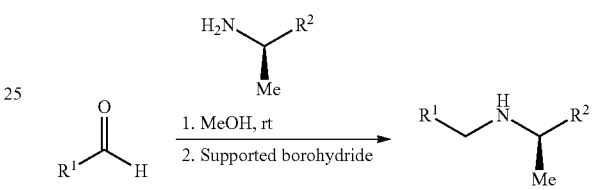

The aldehyde (1 mmol) was dissolved in methanol (1.5 mL), and a solution of the amine (1.2 mmol, 1.2 equiv) in methanol (1.5 mL) was added. The reaction was shaken at rt overnight. Amberlite IRA-400 supported borohydride (0.8 g, 2 mmol, 2 equiv) was added and the mixture was shaken overnight at rt. Aldehyde resin (4-benzyloxybenzaldehyde, polymer-bound; 0.32 g, 0.4 mmol, 0.4 equiv) followed by dichloromethane (2 mL) were added, and the mixture was shaken for another night at rt. The resins were filtered off and washed with MeOH or THF (3×1 mL). The solvents were evaporated under reduced pressure to afford the desired product.

Method E

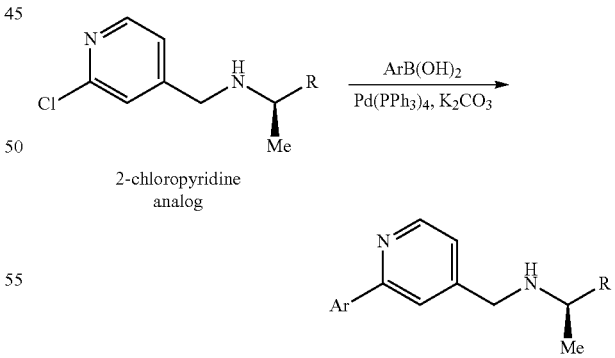

To a solution of 2-chloropyridine analog (1 equiv, prepared by Method C) and aryl boronic acid (1.2 equiv) in 1,2-dimethoxyethane, was added Pd(PPh$_3$)$_4$ (0.1 equiv). The solution was purged with nitrogen and 2 M K$_2$CO$_3$ (3 equiv) in water was added. The reaction mixture was heated to reflux until complete by TLC or HPLC. After cooling to rt, the reaction mixture was partitioned between water and EtOAc. The organic layer was separated and washed with brine (1×), dried over MgSO$_4$, filtered, and concentrated in vacuo. Purification by column chromatography on silica gel gave the desired product. In some instances the product was treated with an excess of 1M HCl in Et$_2$O and evaporated under reduced pressure to afford the HCl salt of the desired product.

Method F

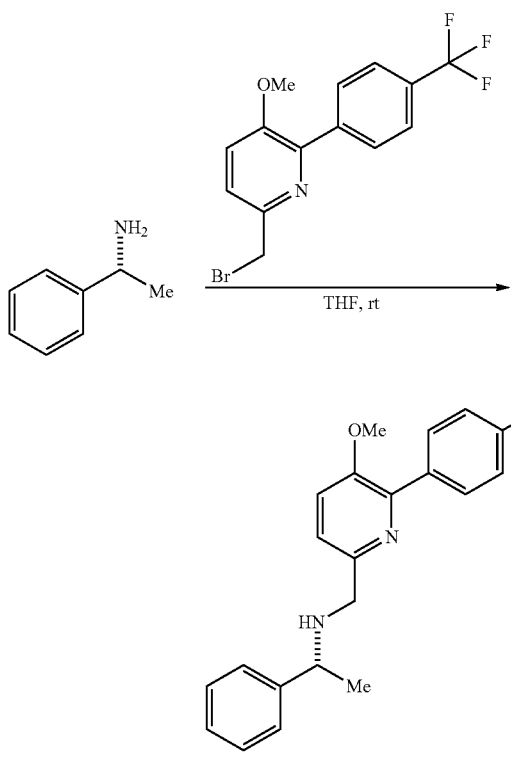

To a solution of 6-(bromomethyl)-3-methoxy-2-(4-(trifluoromethyl)phenyl)pyridine (0.76 g, 0.22 mmol) in THF (10 mL) at rt was added (R)-1-phenylethanamine (0.80 mL, 2.2 mmol). The reaction mixture was stirred at rt for 5 d, diluted with EtOAc, washed with saturated NaHCO$_3$ (1×), brine (1×), dried over MgSO$_4$, filtered, and concentrated. Purification by flash column chromatography on silica gel (70% to 100% EtOAc in hexanes) gave the desired compound. The HCl salt was formed by adding an excess of 1M HCl in diethyl ether to a solution of the free base in diethyl ether and removing the solvent under reduced pressure to yield the HCl salt of (1R)—N-((5-methoxy-6-(4-(trifluoromethyl)phenyl)-2-pyridinyl)methyl)-1-phenylethanamine 3. MS m/z: 387.2 (MH$^+$).

Method G

To a solution of an amine (1.98 mmol) in dry benzene (15 mL) was added aldehyde (1.98 mmol), anhydrous magnesium sulfate (~0.5 g), and a catalytic amount of p-toluenesulfonic acid. The mixture was stirred and heated to 80° C. for 12-24 h. The mixture was filtered through Celite®, concentrated, and dissolved in anhydrous ethanol. The ethanol solution was cooled to 0° C. and sodium borohydride (4.1 mmol) was slowly added. The reaction mixture was warmed to room temperature and stirred for 12-15 h. The reaction mixture was diluted with water and extracted with EtOAc (1×). The organic phase was dried and concentrated. Purification by chromatography on silica gel or crystallization of the HCl salt from an EtOAc and hexanes solution gave the desired product.

Regarding the molecular structures set forth in Methods A-G above, one of skill in the art will readily appreciate that precursors and intermediates having aryl groups other than Cy$^y$=phenyl, e.g. naphthyl, can be used to practice the synthetic methods.

Example 1

Compounds of the invention were synthesized according to the Methods outlined below, as summarized in Table 2

TABLE 2

| STRUCTURE | Starting Amine (Method of synthesis) | NAME | MW | MS m/z (M$^+$ or MH$^+$) |
|---|---|---|---|---|
| 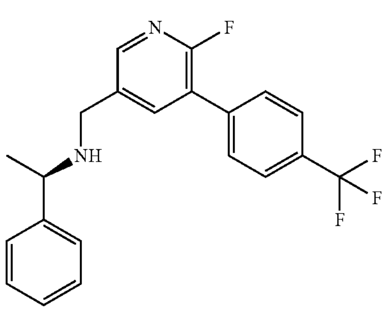 [SMILES: C[C@@H](NCc1cnc(F)c(-c2ccc(C(F)(F)F)cc2)c1)c1ccccc1] | (A) | (1R)-N-((6-fluoro-5-(4-(trifluoromethyl)phenyl)-3-pyridinyl)methyl)-1-phenylethanamine | 374.37 | 375.1 |

TABLE 2-continued

| STRUCTURE | Starting Amine (Method of synthesis) | NAME | MW | MS m/z (M+ or MH+) |
|---|---|---|---|---|
| | (A) | 2'-methoxy-5'-((((1R)-1-phenylethyl)amino)methyl)-N-(tetrahydro-2-furanylmethyl-3,3'-bipyridin-6-amine | 418.53 | 418.6 |
| | (A) | 2'-fluoro-5'-((((1R)-1-phenylethyl)amino)methyl)-N-(tetrahydro-2-furanylmethyl-3,3'-bipyridin-6-amine | 406.50 | 407.2 |
| | (A) | (1R)-N-((6-((6-fluoro-3-pyridinyl)methoxy)-3-pyridinyl)methyl)-1-(1-naphthalenyl)ethanamine | 387.45 | 387.7 |
| | (A) | (1R)-N-((6-((6-fluoro-3-pyridinyl)methoxy)-3-pyridinyl)methyl)-1-phenylethanamine | 337.39 | 337.7 |
| | (A) | (1R)-N-((2-methoxy-6'-(tetrahydro-2-furanylmethoxy)-3,3'-bipyridin-5-yl)methyl)-1-phenylethanamine | 419.52 | 420.0 |

TABLE 2-continued

| STRUCTURE | Starting Amine (Method of synthesis) | NAME | MW | MS m/z (M+ or MH+) |
|---|---|---|---|---|
| | (A) | (1R)-N-((2-methoxy-6'-(2,2,2-trifluoroethoxy)-3,3'-bipyridin-5-yl)methyl)-1-phenylethanamine | 417.42 | 417.8 |
| | (A) | (1R)-N-((2,6'-dimethoxy-3,3'-bipyridin-5-yl)methyl)-1-phenylethanamine | 349.43 | 349.8 |
| | (A) | (1R)-1-(3-chlorophenyl)-N-((6-methoxy-5-(4-(trifluoromethyl)phenyl)-3-pyridinyl)methyl)ethanamine | 420.86 | 420.9 |
| | (A) | (1R)-1-(3-fluorophenyl)-N-((6-methoxy-5-(4-(trifluoromethyl)phenyl)-3-pyridinyl)methyl)ethanamine | 404.40 | 405.0 |
| 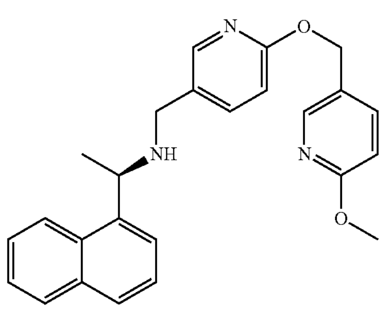 [SMILES: COc1ccc(COc2ccc(CN[C@H](C)c3cccc4ccccc34)cn2)cn1] | (B) | (1R)-N-((6-((6-methoxy-3-pyridinyl)methoxy)-3-pyridinyl)methyl)-1-(1-naphthalenyl)ethanamine | 399.48 | 400.0 |

TABLE 2-continued

| STRUCTURE | Starting Amine (Method of synthesis) | NAME | MW | MS m/z (M+ or MH+) |
|---|---|---|---|---|
| 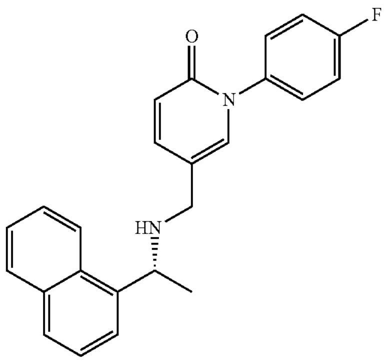 [SMILES: C[C@@H](NCc1ccc(=O)n(-c2ccc(F)cc2)c1)c1cccc2ccccc12] | (C) | 1-(4-Flurophenyl)-5-((((1R)-1-(1-naphthalenyl)ethyl)amino)methyl-2(1H)-pyridinone | 372.43 | 373.2 |
| | (D) | (1R)-1-(1-napthalenyl)-N-(3-pyridinylmethyl)ethanamine | 262.35 | 263.2 |
| | (D) | (1R)-1-(3-methoxyphenyl)-N-(2-pyridinylmethyl)ethanamine | 242.32 | 243.2 |
| | (D) | (1R)-N-((6-methyl-2-pyridinyl)methyl)-1-(1-naphthalenyl)ethanamine | 276.38 | 277.2 |
| | (D) | (1R)-1-(1-naphthalenyl)-N-(3-quinolinylmethyl)ethanamine | 312.41 | 313.2 |
| | (D) | (1R)-1-(3-methoxyphenyl)-N-(2-quinolinylmethyl)ethanamine | 292.37 | 293.2 |

TABLE 2-continued

| STRUCTURE | Starting Amine (Method of synthesis) | NAME | MW | MS m/z (M+ or MH+) |
|---|---|---|---|---|
| (quinolin-3-ylmethyl)-NH-CH(Me)-(3-methoxyphenyl) | (R)-1-(3-methoxyphenyl)ethanamine (D) | (1R)-1-(3-methoxyphenyl)-N-(3-quinolinylmethyl)ethanamine | 292.37 | 293.2 |
| (pyridin-4-ylmethyl)-NH-CH(Me)-(1-naphthyl) | (R)-1-(1-naphthyl)ethanamine (G) | (1R)-1-(1-naphthalenyl)-N-(4-pyridinylmethyl)ethanamine | 262.35 | 263.2 |
| (quinolin-4-ylmethyl)-NH-CH(Me)-(3-methoxyphenyl) | (R)-1-(3-methoxyphenyl)ethanamine (G) | (1R)-1-(3-methoxyphenyl)-N-(4-quinolinylmethyl)ethanamine | 292.37 | 293.2 |
| (pyridin-3-ylmethyl)-NH-CH(Me)-(3-methoxyphenyl) | (R)-1-(3-methoxyphenyl)ethanamine (G) | (1R)-1-(3-methoxyphenyl)-N-(3-pyridinylmethyl)ethanamine | 242.32 | 243.2 |
| (quinolin-2-ylmethyl)-NH-CH(Me)-(1-naphthyl) | (R)-1-(1-naphthyl)ethanamine (D) | (1R)-1-(1-naphthalenyl)-N-(2-quinolinylmethyl)ethanamine | 312.41 | 313.2 |
| (pyridin-2-ylmethyl)-NH-CH(Me)-(1-naphthyl) | (R)-1-(1-naphthyl)ethanamine (G) | (1R)-1-(1-naphthalenyl)-N-(2-pyridinylmethyl)ethanamine | 262.35 | 263.2 |
| (6-methyl-pyridin-2-ylmethyl)-NH-CH(Me)-(3-methoxyphenyl) | (R)-1-(3-methoxyphenyl)ethanamine (D) | (1R)-1-(3-methoxyphenyl)-N-((6-methyl-2-pyridinyl)methyl)ethanamine | 256.34 | 257.2 |

TABLE 2-continued

| STRUCTURE | Starting Amine (Method of synthesis) | NAME | MW | MS m/z (M+ or MH+) |
|---|---|---|---|---|
| (quinolin-3-ylmethyl)-N-[(1R)-1-(4-methylphenyl)ethyl]amine structure | (1R)-1-(4-methylphenyl)ethanamine (D) | (1R)-1-(4-methylphenyl)-N-(3-quinolinylmethyl)ethanamine | 276.38 | 277.2 |
| 6-((4-chlorophenyl)sulfanyl)-pyridin-3-ylmethyl amine with (1R)-1-naphthyl ethyl | (1R)-1-(1-naphthalenyl)ethanamine (D) | (1R)-N-((6-((4-chlorophenyl)sulfanyl)-3-pyridinyl)methyl)-1-(1-naphthalenyl)ethanamine | 404.95 | 405.0 |
| 6-((2-chlorophenyl)sulfanyl)-pyridin-3-ylmethyl amine with (1R)-1-naphthyl ethyl | (1R)-1-(1-naphthalenyl)ethanamine (D) | (1R)-N-((6-((2-chlorophenyl)sulfanyl)-3-pyridinyl)methyl)-1-(1-naphthalenyl)ethanamine | 404.95 | 405.0 |
| (pyridin-2-ylmethyl)-N-[(1R)-1-(4-methylphenyl)ethyl]amine | (1R)-1-(4-methylphenyl)ethanamine (D) | (1R)-1-(4-methylphenyl)-N-(2-pyridinylmethyl)ethanamine | 226.32 | 227.2 |
| 2-(methylsulfanyl)-3-cyano-6-(((1R)-1-phenylethyl)aminomethyl)pyridine | (1R)-1-phenylethanamine (D) | 2-(methylsulfanyl)-6-((((1R)-1-phenylethyl)amino)methyl)-3-pyridinecarbonitrile | 283.39 | 284.2 |
| 2-(methylsulfanyl)-3-cyano-6-(((1R)-1-(3-methoxyphenyl)ethyl)aminomethyl)pyridine | (1R)-1-(3-methoxyphenyl)ethanamine (D) | 6-((((1R)-1-(3-methoxyphenyl)ethyl)amino)methyl)-2-(methylsulfanyl)-3-pyridinecarbonitrile | 313.42 | 314.0 |

TABLE 2-continued

| STRUCTURE | Starting Amine (Method of synthesis) | NAME | MW | MS m/z (M⁺ or MH⁺) |
|---|---|---|---|---|
| (structure) | (structure) (D) | (1R)-N-((6-((4-chlorophenyl)sulfanyl)-3-pyridinyl)methyl)-1-phenylethanamine | 354.90 | 355.0 |
| (structure) | (structure) (D) | (1R)-N-((2-(4-chlorophenoxy)-3-pyridinyl)-methyl)-1-phenylethanamine | 338.83 | 339.2 |
| (structure) | (structure) (C) | (1R)-N-((2-chloro-4-pyridinyl)methyl)-1-(1-naphthalenyl)ethanamine | 296.79 | 297.0 |
| (structure) | (structure) (E) | (1R)-N-((2-(4-methoxyphenyl)-4-pyridinyl)methyl)-1-(1-naphthalenyl)ethanamine | 368.47 | 369.2 |
| (structure) | (structure) (C) | (1R)-N-((2-chloro-4-pyridinyl)methyl)-1-(3-methoxyphenyl)ethanamine | 276.76 | 277.2 |
| (structure) | (structure) (E) | (1R)-N-(2,3'-bipyridin-4-ylmethyl)-1-(1-naphthalenyl)ethanamine | 339.43 | 340.2 |
| (structure) | (structure) (E) | (1R)-1-(3-methoxyphenyl)-N-((2-(4-methoxyphenyl)-4-pyridinyl)methyl)ethanamine | 348.44 | 349.0 |

TABLE 2-continued

| STRUCTURE | Starting Amine (Method of synthesis) | NAME | MW | MS m/z (M⁺ or MH⁺) |
|---|---|---|---|---|
| | (E) | (1R)-N-(2,3'-bipyridin-4-ylmethyl)-1-phenylethanamine | 289.37 | 290.2 |
| | (E) | (1R)-N-((2-(4-methoxyphenyl)-4-pyridinyl)methyl)-1-phenylethanamine | 318.41 | 319.4 |
| | (C) | (1R)-1-(1-naphthalenyl)-N-((6-phenoxy-3-pyridinyl)methyl)ethanamine | 354.44 | 355.2 |
| | (C) | (1R)-1-(3-methoxyphenyl)-N-((6-phenoxy-3-pyridinyl)methyl)ethanamine | 334.41 | 335.2 |
| | (C) | (1R)-N-((9-ethyl-9H-beta-carbolin-3-yl)methyl)-1-(3-methoxyphenyl)ethanamine | 359.46 | 360.2 |
| | (C) | (1R)-N-((9-ethyl-9H-beta-carbolin-3-yl)methyl)-1-phenylethanamine | 329.44 | 330.2 |
| | (C) | (1R)-N-((9-ethyl-9H-beta-carbolin-3-yl)methyl)-1-(1-naphthalenyl)ethanamine | 379.50 | 380.2 |

TABLE 2-continued

| STRUCTURE | Starting Amine (Method of synthesis) | NAME | MW | MS m/z (M+ or MH+) |
|---|---|---|---|---|
| [structure: 1-(4-methoxyphenyl)pyridinone with benzylamine linker] | (R)-1-phenylethylamine (C) | 1-(4-methoxyphenyl)-5-((((1R)-1-phenylethyl)amino)methyl)-2(1H)-pyridinone | 334.41 | 335.2 |
| [structure: 3-chloro-2-(3-fluorophenyl)pyridine with chlorophenyl ethanamine] | (1R)-1-(3-chlorophenyl)ethanamine (F) | (1R)-N-((5-chloro-6-(3-fluorophenyl)-2-pyridinyl)methyl)-1-(3-chlorophenyl)ethanamine | 375.27 | 375.1 |
| [structure: 3-methoxy-2-(3-fluorophenyl)pyridine with chlorophenyl ethanamine] | (1R)-1-(3-chlorophenyl)ethanamine (F) | (1R)-1-(3-chlorophenyl)-N-((6-(3-fluorophenyl)-5-methoxy-2-pyridinyl)methyl)ethanamine | 370.85 | 371.2 |
| [structure: 5-chloro-4-(3-fluorophenyl)pyridine with chlorophenyl ethanamine] | (1R)-1-(3-chlorophenyl)ethanamine (C) | (1R)-N-((5-chloro-4-(3-fluorophenyl)-2-pyridinyl)methyl)-1-(3-chlorophenyl)ethanamine | 375.27 | 375.1 |

Example 2

Biological Activity

The activities of the compounds of the present invention on calcium receptors were measured. In one aspect, the measurement was performed in accordance with the method described in Example 4 of International Publication No. WO 96/12697.

A 4.0-kb NotI-HindIII fragment of the human parathyroid cell $Ca^{2+}$ receptor (hPCaR) cDNA was subcloned into the mammalian expression vector pCEP4 (Invitrogen) containing the hygromycin-resistant gene as a selectable marker. This plasmid was transfected into HEK 293 cells by calcium phosphate precipitation. Transfected cells were grown in Dulbecco's modified Eagle's medium containing 10% fetal bovine serum and hygromycin (200 g/mL). Hygromycin-resistant colonies were subcloned and assayed for hPCaR mRNA by solution hybridization using a $^{32}$P-labeled RNA probe complementary to the (4.0 kb) hPCaR sequence (Garrett, et al., J. Biol. Chem. 270, 12919-12925 (1995)). Clone 7 was used to assess the effects of compounds on $[Ca^{2+}]_i$. This stably transfected cell line is termed HEK 293 4.0-7. For measurements of $[Ca^{2+}]_i$, the cells were recovered from tissue culture flasks by brief treatment with Versene (Invitrogen; containing 0.2 g/L EDTA.4Na in phosphate-buffered saline) and then seeded in collagen coated 384-well plates (BD Biosciences) at 20K cells per well in the growth media (same as above). Cells were grown in 37° C. TC incubator overnight. Then, the media was discarded and cells were loaded with 1× dye from Ca2+ Assay Kit I (BD Biosciences) in parathyroid cell buffer (126 mM NaCl, 4 mM KCl, 1 mM $MgSO_4$, 0.7 mM $K_2HPO_4/KH_2PO_4$, 20 mM HEPES.NaOH (pH 7.45)) containing 0.5% BSA and 1 mM $CaCl_2$. Cells were loaded at room temperature for 90 minutes. Each test compound was added to the cells and the fluorescence was recorded by using excitation and emission wavelengths of 485 and 530 nm, respectively.

The compounds of the invention were tested according to the procedure described above and found to have an $EC_{50}$ of 5 μM or less.

In Vivo Measurements

Male Sprague-Dawley rats weighing 250-400 g were given free access to food and water. Unanesthetized rats were gavaged with an 18-gauge balled needle at a volume between 0.5 and 1 ml. Compounds were formulated in 20% captisol in water at pH 7.0 or 2% hydroxypropyl methylcellulose (HPMC)/1% Tween 80/5% Captisol in water pH 2.0. Calcimimetics were administered at various doses covering the following range 0.03-30 mg/kg in 20% captisol. Vehicle-treated rats received one of the above two vehicles at the maximum volume (0.5-1 ml) used for the calcimimetics. Each rat was bled at time 0 (pre-calcimimetic or vehicle administration) and at various times (1, 2, 4, 8 and 24 h) after oral gavage of calcimimetic or vehicle.

For measurements of blood-ionized $Ca^{2+}$ levels, blood (50 μl was collected from the orbital sinus of anesthetized rats (3% isoflurane in $O_2$) with heparinized capillary tubes. Blood samples were analyzed within seconds of collection using a Rapidlab 348 Blood Gas Analyzer (Bayer HealthCare LLC Diagnostic Division; Tarrytown, N.Y.).

For measurements of serum PTH, phosphorus, a nonheparinized capillary tube was inserted into the orbital sinus and blood (0.5 ml) was collected into SST (clot activator) brand blood tubes. Blood samples were allowed to clot for 15-30 min and centrifuged (3000 rpm; Sorvall RT 600B) at 4° C. Serum was removed and stored below 0° C. until assayed. Serum PTH levels were quantified according to the vendor's instructions using rat PTH immunoradiometric assay kits (Immutopics, San Clemente, Calif.) or rat bioactive intact PTH elisa kit (Immutopics, San Clemente, Calif.). Serum phosphorus levels were determined using a blood chemistry analyzer (AU 400; Olympus, Melville, N.Y.).

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. The compound selected from the group consisting of:
   (1R)-1-(5-methoxy-6-(4-(trifluoromethyl)phenyl)-2-pyridinyl)-N-((1R)-1-phenylethyl)ethanamine,
   (1R)—N-((2-(4-methoxyphenyl)-4-pyridinyl)methyl)-1-(1-naphthalenyl)ethanamine,
   (1R)-1-(3-chlorophenyl)-N-((6-(3-fluorophenyl)-5-methoxy-2-pyridinyl)methyl)ethanamine,
   (1R)-1-(3-methoxyphenyl)-N-((2-(4-methoxyphenyl)-4-pyridinyl)methyl)ethanamine,
   or a pharmaceutically acceptable salt thereof.

2. A pharmaceutical composition comprising the compound of claim 1 or a pharmaceutically acceptable salt thereof and a pharmaceutically acceptable diluent or carrier.

* * * * *